US008652794B2

(12) United States Patent
Squirrell et al.

(10) Patent No.: US 8,652,794 B2
(45) Date of Patent: Feb. 18, 2014

(54) MUTANT LUCIFERASE

(75) Inventors: David J. Squirrell, Salisbury (GB);
Melenie J. Murphy, Salisbury (GB);
Rachel L. Price, Salisbury (GB);
Christopher R. Lowe, Cambridge (GB);
Peter J. White, Cambridge (GB);
Laurence C. Tisi, Cambridge (GB);
James A. H. Murray, Cambridge (GB)

(73) Assignee: Promega Corporation, Madison, WI (US)

( * ) Notice: Subject to any disclaimer, the term of this patent is extended or adjusted under 35 U.S.C. 154(b) by 191 days.

(21) Appl. No.: 13/023,704

(22) Filed: Feb. 9, 2011

(65) Prior Publication Data

US 2011/0177540 A1    Jul. 21, 2011

Related U.S. Application Data

(62) Division of application No. 09/763,824, filed as application No. PCT/GB99/03538 on Oct. 26, 1999, now Pat. No. 7,906,298.

(30) Foreign Application Priority Data

Oct. 28, 1998    (GB) .................................. 9823468.5

(51) Int. Cl.
*C12Q 1/66*    (2006.01)
*C12N 9/02*    (2006.01)

(52) U.S. Cl.
USPC .............................................. 435/8; 435/189

(58) Field of Classification Search
None
See application file for complete search history.

(56) References Cited

U.S. PATENT DOCUMENTS

| 5,049,358 | A |   | 9/1991  | Lau |
|---|---|---|---|---|
| 5,196,524 | A |   | 3/1993  | Gustafson et al. |
| 5,219,737 | A |   | 6/1993  | Kajiyama et al. |
| 5,229,285 | A |   | 7/1993  | Kajiyama et al. |
| 5,480,789 | A |   | 1/1996  | Firoozabady et al. |
| 5,605,793 | A |   | 2/1997  | Stemmer |
| 5,670,356 | A |   | 9/1997  | Sherf et al. |
| 5,674,713 | A |   | 10/1997 | McElroy et al. |
| 5,700,673 | A |   | 12/1997 | McElroy et al. |
| 5,716,851 | A |   | 2/1998  | Pugia et al. |
| 6,074,859 | A | * | 6/2000  | Hirokawa et al. ............. 435/189 |
| 6,132,983 | A |   | 10/2000 | Lowe et al. |
| 6,171,808 | B1 |  | 1/2001  | Squirrell et al. |
| 6,265,177 | B1 |  | 7/2001  | Squirrell et al. |
| 6,387,675 | B1 |  | 5/2002  | Wood et al. |
| 6,602,677 | B1 | * | 8/2003 | Wood et al. ........................ 435/8 |
| 7,183,092 | B2 |  | 2/2007  | Choi et al. |
| 7,241,584 | B2 |  | 7/2007  | Wood et al. |
| 7,452,663 | B2 |  | 11/2008 | Wood et al. |
| 7,732,128 | B2 |  | 6/2010  | Wood et al. |
| 2003/0068801 | A1 |  | 4/2003 | Wood et al. |
| 2003/0232404 | A1 |  | 12/2003 | Wood et al. |
| 2006/0183212 | A1 |  | 8/2006 | Wood et al. |
| 2009/0137019 | A1 |  | 5/2009 | Wood et al. |
| 2009/0311769 | A1 |  | 12/2009 | Wood et al. |
| 2012/0009647 | A1 |  | 1/2012 | Wood et al. |

FOREIGN PATENT DOCUMENTS

| EP | 0337349 | 10/1989 |
|---|---|---|
| EP | 0449621 | 10/1991 |
| EP | 0524448 | 1/1993 |
| EP | 0680515 | 8/1998 |
| EP | 2366778 | 8/2012 |
| GB | 2301592 | 12/1996 |
| GB | 2345913 | 7/2000 |
| JP | 5-244942 | 9/1993 |
| JP | 8-510837 | 11/1996 |
| JP | 9510610 | 10/1997 |
| JP | 9-294600 | 11/1997 |
| JP | 2012161325 | 8/2012 |
| WO | WO 95/18853 | 7/1995 |
| WO | WO 95/25798 | 9/1995 |
| WO | WO 96/02665 | 2/1996 |
| WO | WO 96/22376 | 7/1996 |
| WO | WO 98/13487 | 4/1998 |
| WO | WO 98/46729 | 10/1998 |
| WO | WO 99/14336 | 3/1999 |
| WO | WO 00/24878 | 5/2000 |
| WO | WO 01/20002 | 3/2001 |
| WO | WO 01/31028 | 5/2001 |

OTHER PUBLICATIONS

GenBank Accession No. D25416, Aug. 1997, 2 pages.*
Arslan et al., J. Am. Chem. Soc. 119:10877-10887, 1997.*
United States Patent Office Action for U.S. Appl. No. 10/111,723 dated Feb. 16, 2011 (15 pages).
United States Patent Office Action for U.S. Appl. No. 12/462,320 dated Feb. 2, 2011 (22 pages).
United States Patent Office Action for U.S. Appl. No. 12/462,320 dated Jun. 9, 2011 (4 pages).
United States Patent Office Action for U.S. Appl. No. 10/111,723 dated Aug. 2, 2011 (14 pages).
European Patent Office Action for Application No. 10179370.1 dated Aug. 22, 2011 (14 pages).

(Continued)

*Primary Examiner* — David J Steadman
(74) *Attorney, Agent, or Firm* — Michael Best & Friedrich LLP

(57) ABSTRACT

An isolated recombinant luciferase having luciferase activity. The recombinant luciferase has an amino acid sequence which differs from the wild-type luciferase from *Photinus pyralis, Luciola mingrelica, Luciola cruciata, Luciola lateralis, Hotaria parvula, Pyrophorus plagiophthalamus, Lampyris noctiluca, Pyrocoelia miyako* or *Photinus pennsylvanica*. In the sequence of the recombinant luciferase, the amino acid residue corresponding to phenylalanine 295 in *Photinus pyralis* wild-type luciferase or to leucine 297 in *Luciola mingrelica, Luciola cruciata* or *Luciola lateralis* wild-type luciferases, is mutated compared to the corresponding amino acid which appears in the corresponding wild-type luciferase sequence. The recombinant luciferase has increased thermostability compared to the corresponding wild-type luciferase.

15 Claims, 8 Drawing Sheets

(56) References Cited

OTHER PUBLICATIONS

European Patent Office Action for Application No. 10179372.7 dated Aug. 22, 2011 (14 pages).
European Patent Office Action for Application No. 10179373.5 dated Aug. 22, 2011 (14 pages).
European Patent Office Action for Application No. 10179358.6 dated Aug. 22, 2011 (14 pages).
European Patent Office Action for Application No. 10179359.4 dated Aug. 22, 2011 (15 pages).
European Patent Office Action for Application No. 10179361.0 dated Aug. 22, 2011 (14 pages).
European Patent Office Action for Application No. 08013254.1 dated Aug. 16, 2011 (4 pages).
Alberts, B. et al., Molecular Biology of the Cell, Third Edition, Garland Publishing, Inc. (1994) 56-57.
Arkin, A.P. et al., "Optimizing nucleotide mixtures to encode specific subsets of amino acids for semi-random mutagenesis," BioTechnology (1992) 10:297-300.
Arnold, F.H., "Directed evolution: creating biocatalysts for the future," Chem. Eng. Sci. (1996) 51:5091-5102.
Arslan, T. et al., "Structurally modified *Firefly luciferase*. Effects of amino acid substitution at position 286," J. Amer. Chem. Soc. (1997) 119(45):10877-10887.
Barnes, W.M., "Variable patterns of expression of luciferase in transgenic tobacco leaves," Proc. Natl. Acad. Sci. USA (1990) 87:9183-9197.
Bowie et al., "Deciphering the message in protein sequences tolerance to amino acid substitutions," Science (1990) 247:1306-1310.
Branden, C. et al., "Introduction to protein structure," Garland Publishing Inc., New York (1991) 247.
Cadwell, R.C. et al., "Randomization of genes by PCR mutagenesis," PCR Methods and Applications (1992) 2:28-33.
Climie, S. et al., "Saturation site-directed mutagenesis of thymidylate synthase," J. Biol. Chem. (1990) 265(31): 18776-18779.
Conti, E. et al., "Crystal structure of *Firefly luciferase* throws light on a superfamily of adenylate-forming enzymes," Structure (1996) 4(3):287-298.
De Wet, J.R. et al., "*Firefly luciferase* gene: structure and expression in mammalian cells," Mol. Cell. Biol. (1987) 7(2):725-737.
Dementieva, E.I. et al., "Assay of ATP in intact *Escherichia coli* cells expressing recombinant *Firefly luciferase*," Biochem. (1996) 61(7):915-920.
Dementieva, E.I., "Physiocochemical properties of recombinant luciolo *Mingrelica luciferase* and its mutant forms," Biochem. (1996) 61(1):115-119.
Devereux, J. et al., "A comprehensive set of sequence analysis programs for the VAX," Nucl. Acids Res. (1984) 12(1):38-395.
Devine, J.H. et al., "Luciferase from the East European firefly *Luciola mingrelica*: cloning and nucleotide sequence of the cDNA, overexpression in *Escherichia coli* and purification of the enzyme," Biochimica et Biophysica Acta (1993) 1173:121-132.
Fromant, M. et al., "Direct random mutagenesis of gene-sized DNA fragments using polymerase chain reaction," Anal. Biochem. (1995) 224(1):347-353.
Hanahan, "Techniques for transformation of *E. coli*," In: DNA Cloning: A Practical Approach, Glover, D.W. editor, IRL Press, Oxford (1985) 1(6):109-135.
Huang, W. et al., "Identification of biologically active mutants by combinatorial cassette mutagenesis: exclusion of wild-type codon from degenerate codons," Anal. Biochem. (1994) 218(2):454-457.
Janowski, M., "Ras proteins and the Ras-related signal transduction pathway," Radiation & Env. Biophys. (1991) 30(3):185-189.
Kajiyama, N. et al., "Thermostabilization of *Firefly luciferase* by a single amino acid substitution at position 217," Biochem. (1993) 32(50):13795-13799.
Kajiyama, N. et al., "Enhancement of thermostability of forefly luciferase from *Luciola lateralis* by a single amino acid substitution," Biosci. Biotech. Biochem. (1994) 58(6):1170-1171.
Kajiyama, N. et al., "Isolation and characterization of mutants of *Firefly luciferase* which produce different colors of light," Protein Eng. (1991) 4(6):691-693.
Kim-Choi, E. et al., "Creating a mutant luciferase resistant to HPV chemical inhibition by random mutagenesis and colony-level screening," Luminescence (2006) 21:135-142.
Kim-Choi, E. et al., "Kinetic characterization and in vitro toxicity evaluation of a luciferase less susceptible to HPV chemical inhibition," Toxicology in Vitro (2006) 20:1537-1547.
Klock, C., "Cloning vector pGEM-luc," Promega Corporation, Accession No. X65316 (Apr. 7, 1992) 5 pages.
Kutuzova et al., "Bioluminescence color variation and kinetic behavior relationships among beetle luciferases," Bioluminescence & Chemiluminescence, Molecular Reporting with Photons, J.W. Hastings et al. editors, John Wiley & Sons (1996) 248-252.
Law, G.H. et al., "Mutagenesis of solvent-exposed amino acids of *Photinus pyralis* luciferase improves thermostability and pH tolerance," Biochem. J. (2006) 397:305-312.
Lipman, D. et al., "Rapid and sensitive protein similarity searches," Science (1985) 227:1435-1441.
Liu, Y. et al., "Factors influencing the efficiency of cationic liposome-mediated intravenous gene delivery," Nature Biotech. (1997) 15:167-173.
Manukhov et al., "Cloning of the vibrio harveyi luxA and luxB genes and the expression fo bioluminescence in *Escherichia coli* and *Bacillus subtillis*," Russian Biotech. (1996) 1:1-6.
Ohmiya, Y. et al., "Cloning, expression and sequence analysis of cDNA for the luciferases from the Japanese fireflies, *Pyrocoelia miyako* and *Hotaria parvula*," Photochem. Photobiol. (1995) 62(2):309-313—Genbank Accession No. Q26076, Oct. 2006 (2 pages).
Purdy et al., "Heterologous gene expression in *Campylobacter coli*: the use of bacterial luciferase in a promoter probe vector," FEMS Microbiology Letters (1993) 111:233-237.
Qiagen Distributors, "QIAprep® Miniprep Handbook," (Mar. 2002) 1-48.
Reeck, G.R. et al., "'Homology' in proteins and nucleic acids: a terminology muddle and a way out of it," Cell (1987) 50:667.
Rommens, J.M. et al., "cAMP-inducible chloride conductance in mouse fibroblast lines stably expressing the human cystic fibrosis transmembrance conductance regulator," Proc. Natl. Acad. Sci. USA (1991) 88:7500-7504.
Saiki, R.K. et al., "Primer-directed enzymatic amplification of DNA with a thermostable DNA polymerase," Science (1988) 239:487-491.
Sala-Newby, G.B., "Sequence and biochemical similarities between the luciferases of the glow-worm *Lampyris noctiluca* and the firefly *Photinus pyralis*," Biochem. J. (1996) 313:761-767.
Sala-Newby, G.B. et al., "Engineering a bioluminescent indicator for cyclic AMP-dependent protein kinase," Biochem. J. (1991) 279:727-732.
Sala-Newby, G.B. et al., "Engineering *Firefly luciferase* as an indicator of cyclic AMP-dependent protein kinase in living cells," FEBS Lett. (1992) 307(2):241-244.
Sambrook, J. et al., "Molecular Cloning—A Laboratory Manual," Second Edition (1989) 17.37-17.39.
Sanger, F. et al., "DNA sequencing with chain-terminating inhibitors," Proc. Natl. Acad. Sci. (1977) 74(12):5463-5467.
Steghens, J. et al., "*Firefly luciferase* has two nucleotide binding sites: effect of nucleoside monophosphate and CoA on the light-emission spectra," Biochem. J. (1998) 336:109-113.
Stemmer, W.P.C., "DNA shuffling by random fragmentation and reassembly: in vitro recombination for molecular evolution," Proc. Natl. Acad. Sci. USA (1994) 91:10747-10751.
Strause, L.G. et al., "Characteristics of luciferases from a variety of firefly species: evidence for the presence of luciferase isozymes," Insect Biochem. (1981) 11(4):417-422.
Sung, D. et al., "The N-terminal amino acid sequences of the *Firefly luciferase* are important for the stability of the enzyme," Photochem. Photobiol. (1998) 68:749-753.
Szittner et al., "Nucleotide sequence, expression, and properties of luciferase coded by lux genes froma terrestrial bacterium," J. Biol. Chem. (1990) 265(27):16581-16587.

(56) References Cited

OTHER PUBLICATIONS

Thompson, J.F. et al., "Modulation of *Firefly luciferase* stability and impact on studies of gene regulation," Gene (1991) 103:171-177.
Thompson, J.F. et al., "Mutation of a protease-sensitive region in *Firefly luciferase* alters light emission properties," J. Biol. Chem. (1997) 272:18766-18771.
Tisi, L.C. et al., "The basis of the bathochromic shift in the luciferase from *Photinus pyralis*," Biolumin. Chemilumin.: Proceedings of the Symposium on Bioluminescence and Chemiluminescence, 12th, Cambridge, United Kingdom (Apr. 5-9, 2002) 57-60.
Tisi, L.C., "Development of a thermostable *Firefly luciferase*," Anal. Chim. Acta (2002) 457:115-123.
Viviani, V. et al., "Cloning, sequence analysis, and expression of active phrixothrix railroad-worms luciferases: relationship between bioluminescence spectra and primary structures," Biochem. (1999) 38:8271-8279.
Watson, J. et al., Molecular Biology of the Gene, Fourth Edition, The Benjamin/Cummings Publishing Company, vol. 1—General Principles (1987) 43.
White, P.J. et al., "Generation and characterisation of a thermostable mutant of luciferase from *Photinus pyralis*," Proceedings of the 8th International Symposium on Bioluminescence & Chemiluminescence, Sep. 1994, Biolum. Chemilum. (1994) 419-422.
White, P.J. et al., "Improved thermostability of the North American *Firefly luciferase*: saturation mutagenesis at postion 354," Biochem. J. (1996) 319(Pt. 2):343-350.
Willey, T. et al., "Design and selection of *Firefly luciferases* with novel in vivo and in vitro properties," Proceedings of the 11th International Symposium on Bioluminescence and Chemiluminescence (Sep. 6-10, 2000) 201-204.
Witkowski, A. et al., "Conversion of a B-ketoacyl synthase to a malonyl decarboxylase by replacement of the active-site cysteine with glutamine," Biochem. (1999) 38:11643-11650.
Wood, K.V. et al., "Complementary DNA coding click beetle luciferases can elicit bioluminescence of different colors," Science (1989) 244:700-702.
Wood, K.V., "The chemical mechanism and evolutionary development of beetle bioluminescence," Photochem. Photobiol. (1995) 62(4):662-673.
Wood, K.V. et al., "Introduction to beetle luciferases and their applications," J. Biolum. Chemilum. (1989) 4:289-301.
Wood, K.V., "Luc genes: introduction of colour into bioluminescence assays," J. Biolumin. Chemilumin. (1990) 5:107-114.
Wood, K.V. et al., "Photographic detection of luminescence in *Escherichia coli* containing the gene for *Firefly luciferase*," Anal. Biochem. (1987) 161:501-507.
Wood, K.V. et al., "Bioluminescent click beetles revisited," J. Biolumin. Chemilumin. (1989) 4:31-39.
Ye, L., "Cloning and sequencing of a cDNA for *Firefly luciferase* from *Photuris Pennsylvanica*," Biochimica et Biophysica Acta (1997) 1339(1):39-52.
Zenno, S. et al., "Firefly mRNA for luciferase, complete cds, clone pPFL19," Database EMBL Accession No. D25415 (1996) 2 pages.
Zhang, J. et al., "Directed evolution of a fucosidase from a galactosidase by DNA shuffling and screening," Proc. Natl. Acad. Sci. (1997) 94(9):4504-4509.
International Preliminary Examination Report for Application No. PCT/GB96/00099 dated Apr. 10, 1997 (5 pages).
Written Opinion for Application No. PCT/GB96/00099 dated Oct. 24, 1996 (3 pages) excerpts (all that is in file).
International Search Report for Application No. PCT/GB96/00099 dated May 9, 1996 (3 pages).
International Preliminary Examination Report for Application No. PCT/GB98/01026 dated Jun. 29, 1999 (5 pages).
International Search Report for Application No. PCT/GB98/01026 dated Oct. 13, 1998 (4 pages).
Written Opinion for Application No. PCT/GB98/01026 dated Feb. 5, 1999 (6 pages).
International Preliminary Examination Report for Application No. PCT/GB99/003538 dated Aug. 14, 2000 (4 pages).
International Search Report for Application No. PCT/GB99/003538 dated May 23, 2000 (5 pages).
Invitation to Pay Additional Fees and Partial International Search Report for Application No. PCT/GB99/003538 dated Mar. 20, 2000 (5 pages).
International Preliminary Examination Report for Application No. PCT/GB00/004133 dated May 30, 2002 (11 pages).
Written Opinion for Application No. PCT/GB00/004133 dated Apr. 11, 2002 (10 pages).
International Search Report for Application No. PCT/GB00/004133 dated Aug. 1, 2001 (4 pages).
International Preliminary Examination Report for Application No. PCT/GB1995/000629 dated Jul. 12, 1996 (4 pages).
Written Opinion for Application No. PCT/GB1995/000629 dated Dec. 15, 1995 (3 pages).
International Search Report for Application No. PCT/GB1995/000629 dated Aug. 1, 1995 (3 pages).
International Preliminary Examination Report for Application No. PCT/US98/19494 dated Jan. 11, 2000 (8 pages).
International Search Report for Application No. PCT/US98/19494 dated Apr. 16, 1999 (5 pages).
Written Opinion for Application No. PCT/US98/19494 dated Sep. 14, 1999 (9 pages).
International Search Report for Application No. PCT/US95/00108 dated Apr. 17, 1995 (3 pages).
International Search Report for Application No. PCT/US99/30925 dated Aug. 14, 2000 (10 pages).
Invitation to Pay Additional Fees and Partial Search Report for Application No. PCT/US99/30925 dated Jun. 2, 2000 (12 pages).
United States Patent Office Action for U.S. Appl. No. 08/875,277 dated Dec. 17, 1999 (8 pages).
United States Patent Office Action and Notice of Allowance for U.S. Appl. No. 08/875,277 dated Jul. 3, 2000 (4 pages).
United States Patent Office Action for U.S. Appl. No. 08/875,277 dated Dec. 7, 1998 (9 pages).
United States Patent Office Action for U.S. Appl. No. 08/875,277 dated Jul. 6, 1998 (10 pages).
United States Patent Office Action/Notice of Allowance for U.S. Appl. No. 09/380,061 dated Mar. 5, 2001 (5 pages).
United States Patent Office Action for U.S. Appl. No. 09/763,824 dated Nov. 9, 2009 (9 pages).
United States Patent Office Action for U.S. Appl. No. 09/763,824 dated Jun. 24, 2008 (15 pages).
United States Patent Office Action for U.S. Appl. No. 09/763,824 dated Nov. 28, 2007 (20 pages).
United States Patent Office Action for U.S. Appl. No. 09/763,824 dated Apr. 3, 2007 (16 pages).
United States Patent Office Action for U.S. Appl. No. 09/763,824 dated May 16, 2006 (14 pages).
United States Patent Office Action for U.S. Appl. No. 09/763,824 dated Sep. 19, 2005 (18 pages).
United States Patent Office Action for U.S. Appl. No. 09/763,824 dated Dec. 15, 2004 (27 pages).
United States Patent Office Action for U.S. Appl. No. 09/763,824 dated Jul. 22, 2010 (9 pages).
United States Patent Office Action for U.S. Appl. No. 09/763,824 dated Sep. 30, 2010 (3 pages).
United States Patent Office Notice of Allowance for U.S. Appl. No. 09/763,824 dated Nov. 8, 2010 (5 pages).
United States Patent Office Action for U.S. Appl. No. 10/111,723 dated Feb. 22, 2010 (15 pages).
United States Patent Office Action for U.S. Appl. No. 10/111,723 dated Oct. 9, 2009 (11 pages).
United States Patent Office Action for U.S. Appl. No. 10/111,723 dated Aug. 6, 2008 (25 pages).
United States Patent Office Action for U.S. Appl. No. 10/111,723 dated Mar. 12, 2008 (16 pages).
United States Patent Office Action for U.S. Appl. No. 10/111,723 dated Jul. 20, 2007 (27 pages).
United States Patent Office Action for U.S. Appl. No. 10/111,723 dated Dec. 1, 2006 (31 pages).

(56) References Cited

OTHER PUBLICATIONS

United States Patent Office Action for U.S. Appl. No. 10/111,723 dated Dec. 19, 2005 (20 pages).
United States Patent Office Action for U.S. Appl. No. 10/111,723 dated May 24, 2004 (22 pages).
United States Patent Office Action for U.S. Appl. No. 10/111,723 dated Sep. 20, 2010 (6 pages).
United States Patent Office Action for U.S. Appl. No. 08/718,425 dated Jun. 7, 1999 (8 pages).
United States Patent Office Notice of Allowance for U.S. Appl. No. 08/718,425 dated Nov. 12, 1999 (6 pages).
United States Patent Office Action for U.S. Appl. No. 08/718,425 dated Mar. 13, 1998 (8 pages).
United States Patent Office Action for U.S. Appl. No. 08/718,425 dated Jun. 18, 1997 (10 pages).
United States Patent Office Action for U.S. Appl. No. 08/718,425 dated Apr. 15, 1997 (10 pages).
United States Patent Office Advisory Action for U.S. Appl. No. 09/156,946 dated May 2, 2001 (5 pages).
United States Patent Office Action for U.S. Appl. No. 09/156,946 dated Oct. 24, 2000 (8 pages).
United States Patent Office Action for U.S. Appl. No. 09/156,946 dated Apr. 26, 2000 (10 pages).
United States Patent Office Action for U.S. Appl. No. 09/838,469 dated Sep. 10, 2002 (9 pages).
United States Patent Office Action for U.S. Appl. No. 09/396,154 dated Jan. 2, 2002 (9 pages).
United States Patent Office Action for U.S. Appl. No. 09/396,154 dated Jul. 3, 2001 (10 pages).
United States Patent Office Action for U.S. Appl. No. 09/396,154 dated Jul. 16, 2002 (4 pages).
United States Patent Office Action for U.S. Appl. No. 10/378,168 dated Oct. 12, 2006 (13 pages).
United States Patent Office Action for U.S. Appl. No. 10/378,168 dated Feb. 9, 2006 (18 pages).
United States Patent Office Action for U.S. Appl. No. 11/291,644 dated Jan. 26, 2009 (13 pages).
United States Patent Office Action for U.S. Appl. No. 11/291,644 dated Jul. 8, 2008 (18 pages).
United States Patent Office Action for U.S. Appl. No. 11/811,898 dated Sep. 17, 2009 (23 pages).
Australian Patent Office Action for Application No. 63573/99 dated May 23, 2003 (2 pages).
Australian Patent Office Action for Application No. 63573/99 dated May 13, 2002 (3 pages).
Australian Patent Office Action for Application No. 2004200277 dated Jul. 7, 2005 (1 page).
Australian Patent Office Action for Application No. 2004202276 dated Jul. 21, 2006 (2 pages).
Australian Patent Office Action for Application No. 2004202277 dated Dec. 20, 2007 (1 page).
Australian Patent Office Action for Application No. 2004202277 dated Jul. 21, 2006 (2 pages).
Canadian Patent Office Action for Application No. 2342300 dated Jul. 28, 2008 (2 pages).
Canadian Patent Office Action for Application No. 2342300 dated Nov. 22, 2007 (3 pages).
European Patent Office Action for Application No. 99950990.4 dated Oct. 11, 2007 (11 pages).
European Patent Office Action for Application No. 99950990.4 dated Sep. 16, 2005 (7 pages).
European Patent Office Action for Application No. 99950990.4 dated Apr. 6, 2004 (5 pages).
European Patent Office Action for Application No. 99950990.4 dated Jul. 2, 2003 (5 pages).
European Patent Office Action for Application No. 99950990.4 dated May 7, 2003 (5 pages).
European Patent Office Action for Application No. 04000812.0 dated Oct. 11, 2007 (10 pages).
European Patent Office Action for Application No. 04000812.0 dated Sep. 16, 2005 (5 pages).
European Patent Search Report for Application No. 04000812.0 dated Apr. 6, 2005 (6 pages).
European Patent Search Report for Application No. 04000812.0 dated Jan. 27, 2005 (5 pages).
European Patent Search Report for Application No. 08013254.1 dated Sep. 10, 2009 (19 pages).
Great Britain Patent Office Action for Application No. 9925162.1 dated Oct. 22, 2003 (4 pages).
Great Britain Patent Office Action for Application No. 9925162.1 dated Mar. 31, 2003 (3 pages).
Japanese Patent Office Action for Application No. 2000-578432 dated Aug. 31, 2009 (10 pages) with English translation.
Japanese Patent Office Action for Application No. 2000-578432 dated Aug. 16, 2010 (26 pages) with English translation.
Japanese Patent Office Action for Application No. 2000-578432 dated Dec. 5, 2011 (19 pages).
European Patent Office Action for Application No. 08013254.1 dated Jan. 26, 2012 (6 pages).
United States Patent Office Action for U.S. Appl. No. 13/213,457 dated Jun. 21, 2012 (21 pages).
English Translation of an interview with the Japanese Examiner for Application No. 2000-578432 dated Aug. 21, 2012 (1 page).
Japanese Patent Office Action for Application No. 2000-578432 dated Aug. 27, 2012 (3 pages) with English Translation.
Japanese Patent Office Action for Application No. 2011-031071 dated Sep. 13, 2012 (9 pages) with English Translation.
United States Patent Office Action for U.S. Appl. No. 13/213,457 dated Mar. 7, 2013 (18 pages).
United States Patent Office Action for U.S. Appl. No. 10/111,723 dated May 14, 2013 (16 pages).
Japanese Patent Office Action for Application No. 2011-031071 dated Oct. 29, 2013 (7 pages with English Translation).
United States Patent Office Action for U.S. Appl. No. 13/213,457 dated Oct. 19, 2013 (19 pages).
United States Patent Office Notice of Allowance for U.S. Appl. No. 10/111,723 dated Nov. 5, 2013 (14 pages).

* cited by examiner

Fig. 5.

| | |
|---|---|
| CGCCGGTGAGCTCCCCGCCGCCG | SACI-SENSE / 6371 |
| CGGCGGCGGGGAGCTCACCGGCG | SACI-ANTI / 6372 |
| CGAACACTTCTTCATCGTTGACCGCCTTAAGTCTTTAATTAAATACAAAGG | AFLII-SENSE / 6373 |
| CCTTTGTATTTAATTAAAGACTTAAGGCGGTCAACTATGAAGAAGTGTTCG | AFLII-ANTI / 6374 |
| GAAAGGCCCGGCACCAGCCTATCCTCTAGAGG | F14A-SENSE / 6375 |
| CCTCTAGCGGATAGGCTGGTGCCGGGCCTTTC | F14A-ANTI / 6376 |
| CCATAAATTTACCGAATTCGTCGACTTCGATCGAGG | C-TERM_SEQ / 6641 |
| GTGTGGAATTGTGAGCGG | N-TERM_SEQ / 6651 |
| GAGATACGCCGCGGTTCCTGG | L35A-SENSE / 6652 |
| CCAGGAACCGCGGCGTATCTC | L35A-SENSE / 6653 |

| | |
|---|---|
| CCCTATTTTCATTCCTGGCCAAAAGCACTG | F295L-SENSE / 9048 |
| GAGTGCTTTTGGCCAGGAATGAAAATAGGG | F295L-ANTI / 9049 |
| CCGCATAGAgCTCTCTGCGTCAGATTC | T214A + A215L-SENSE / 9063 |
| GAATCTGACGCAGAGAGcTCTATGCGG | T214A + A215L-ANTI / 9064 |
| GTTGACCGCTTGGGATCCTTAATTAAATAC | Insertion of BamHI at G339 / 9077 |

| | |
|---|---|
| GTATAGATTTGAAAAAGAGCTG | E270K-SENSE / 257 |
| CAGCTCTTTTTCAAATCTATAC | E270K-ANTI / 258 |
| GGCTACATACTGGAGACATAGC | S420T-SENSE / 629 |
| GCTATGTCTCCAGTATGTAGCC | S420T-ANTI / 630 |
| GCAGTTGCGCCCGTGAACGAC | A105L-SENSE / 790 |
| GTCGTTCACGGGCGCAACTGC | A105L-ANTI / 791 |
| CAAATCATTCCGGGTACTGCGATTTTAAG | D234G-SENSE / 792 |
| CTTAAAATCGCAGTACCCGGAATGATTTG | D234G-ANTI / 793 |

| | |
|---|---|
| CCGCATAGAACTCTCTGCGTCAGATTC | A215L-SENSE / 7726 |
| GAATCTGACGCAGAGAGTTCTATGCGC | A215L-ANTI / 7727 |
| CTGATTACACCCAAGGGGGATG | E354K-SENSE / 7792 |
| CATCCCCCTTGGGTGTAATCAG | E354K-ANTI / 7793 |
| ccettccgcatagannnngcctgcgtcagt | T214N-Sense / 8202 |
| actgacgcaggcNNNtctatgcggaaggg | T214N-Anti / 82033 |

| | |
|---|---|
| GCAATCAAATCGCTCCGGATACTGC | I232A-SENSE / 6911 |
| GCAGTATCCGGAGCGATTTGATTGC | I232A-ANTI / 6912 |

| | |
|---|---|
| CCATTCCATCAAGGTTTTGG | H245Q-SENSE / 9128 |
| CCAAAACCTTGATGGAATGG | H245Q-ANTI / 9129 |

MUTANT LUCIFERASE

CROSS-REFERENCE TO RELATED APPLICATIONS

This application is a divisional of U.S. patent application Ser. No. 09/763,824, filed Feb. 27, 2001, which is a national stage filing under 35 USC 371 of International Application No. PCT/GB99/03538, filed Oct. 26, 1999, which claims priority benefits to United Kingdom Patent Application No. 9823468.5, filed Oct. 28, 1998. These applications are incorporated herein by reference in their entirety.

SUMMARY

The present invention relates to novel proteins, in particular mutant luciferase enzymes having increased thermostability as compared to the corresponding wild type enzyme, to the use of these enzymes in assays and to test kits containing them.

Firefly luciferase catalyses the oxidation of luciferin in the presence of ATP, $Mg^{2+}$ and molecular oxygen with the resultant production of light. This reaction has a quantum yield of about 0.88. The light emitting property has led to its use in a wide variety of luminometric assays where ATP levels are being measured. Examples of such assays include those which are based upon the described in EP-B-680515 and WO 96/02665.

Luciferase is obtainable directly from the bodies of insects, in particular beetles such as fireflies or glow-worms. Particular species from which luciferases have been obtained include the Japanese GENJI or KEIKE fireflies, *Luciola cruciata* and *Luciola lateralis*, the East European firefly *Luciola mingrelica*, the North American firefly *Photinus pyralis* and the glow-worm *Lampyris noctiluca*. Other species from which luciferase can be obtained are listed in Ye et al., Biochimica et Biophysica Acta, 1339 (1997) 39-52. Yet a further species is *Phrixothrix* (railroad-worms), as described by Viviani et al., Biochemistry, 38, (1999) 8271-8279.

However, since many of the genes encoding these enzymes have been cloned and sequenced, they may also be produced using recombinant DNA technology. Recombinant DNA sequences encoding the enzymes are used to transform microorganisms such as *E. coli* which then express the desired enzyme product.

The heat stability of wild and recombinant type luciferases is such that they lose activity quite rapidly when exposed to temperatures in excess of about 30° C., particularly over 35° C. This instability causes problems when the enzyme is used or stored at high ambient temperature, or if the assay is effected under high temperature reaction conditions, for example in order to increase reaction rate.

Mutant luciferases having increased thermostability are known from EP-A-524448 and WO95/25798. The first of these describes a mutant luciferase having a mutation at position 217 in the Japanese firefly luciferase, in particular by replacing a threonine residue with an isoleucine residue. The latter describes mutant luciferases having over 60% similarity to luciferase from *Photinus pyralis*, *Luciola mingrelica*, *Luciola cruciata* or *Luciola lateralis* but in which the amino acid residue corresponding to residue 354 of *Photinus pyralis* or 356 of the *Luciola* species is mutated such that it is other than glutamate.

The applicants have found yet further mutants which can bring about increased thermostability and which may complement the mutations already known in the art.

The present invention provides a protein having luciferase activity and at least 60% similarity to luciferase from *Photinus pyralis*, *Luciola mingrelica*, *Luciola cruciata* or *Luciola lateralis*, *Hotaria paroula*, *Pyrophorus plagiophthalamus Lampyris noctiluca*, *Pyrocoelia nayako*, *Photinus pennsylanvanica* or *Phrixothrix*, wherein in the sequence of the enzyme, at least one of (a) the amino acid residue corresponding to residue 214 in *Photinus pyralis* luciferase or to residue 216 of *Luciola mingrelica*, *Luciola cruciata* or *Luciola lateralis* luciferase;

(b) the amino acid residue corresponding to residue 232 in *Photinus pyralis* luciferase or to residue 234 of *Luciola mingrelica*, *Luciola cruciata* or *Luciola lateralis* luciferase;

(c) the amino acid residue corresponding to residue 295 in *Photinus pyralis* luciferase or to residue 297 of *Luciola mingrelica*, *Luciola cruciata* or *Luciola lateralis* luciferase;

(d) the amino acid residue corresponding to amino acid 14 of the *Photinus pyralis* luciferase or to residue 16 of *Luciola mingrelica*, 6 residue 17 of *Luciola cruciata* or *Luciola lateralis*;

(e) the amino acid residue corresponding to amino acid 35 of the *Photinus pyrails* luciferase or to residue 37 of *Luciola mingrelica* 38 of *Luciola cruciata* or *Luciola lateralis*;

(f) the amino acid residue corresponding to amino acid residue 105 of the *Photinus pyralis* luciferase or to residue 106 of *Luciola mingrelica*, 107 of *Luciola cruciata* or *Luciola lateralis* or 108 of *Luciola lateralis* gene;

(g) the amino acid residue corresponding to amino acid residue 234 of the *Photinus pyralis* luciferase or to residue 236 of *Luciola mingrelica*, *Luciola cruciata* or *Luciola lateralis*;

(h) the amino acid residue corresponding to amino acid residue 420 of the *Photinus pyralis* luciferase or to residue 422 of *Luciola mingrelica*, *Luciola cruciata* or *Luciola lateralis*;

(i) the amino acid residue corresponding to amino acid residue 310 of the *Photinus pyralis* luciferase or to residue 312 of *Luciola mingrelica*, *Luciola cruciata* or *Luciola lateralis*; is different to the amino acid which appears in the corresponding wild type sequence and wherein the luciferase enzyme possesses has increased thermostability as compared to an enzyme having the amino acid of the corresponding wild-type luciferase of a particular species at this position.

Preferably, the protein has luciferase activity and at least 60% similarity to luciferase from *Photinus pyralis*, *Luciola mingrelica*, *Luciola cruciata* or *Luciola lateralis*, *Hotaria paroula*, *Pyrophorus plagiophthalamus Lampyris noctiluca*, *Pyrocoelia nayako*, or *Photinus pennsylanvanica*.

In particular, the protein is a recombinant protein which has luciferase activity and substantially the sequence of a wild-type luciferase, for example of *Photinus pyralis*, *Luciola mingrelica*, *Luciola cruciata* or *Luciola lateralis*, *Hotaria paroula*, *Pyrophorus plagiophthalamus* (Green-Luc GR), *Pyrophorus plagiophthalamus* (Yellow-Green Luc YG), *Pyrophorus plaglophthalamus* (Yellow-Luc YE), *Pyrophorus plagiophthalamus*

(Orange-Luc OR), *Lampyris noctiluca*, *Pyrocelia nayako* *Photinus pennsylanvanica* LY, *Photinus* pennsylanvanica KW, Photinus pennsylanvanica J19, or *Phrixothrix* green ($Pv_{GR}$) or red ($Ph_{RE}$) but which may include one or more, for example up to 100 amino acid residues, preferably no more than 50 amino acids and more preferably no more than 30 amino acids, which have been engineered to be different to that of the wild type enzyme.

In particular, bioluminescent enzymes from species that can use the substrate D-luciferin (4,5-dihydro-2-(6-hydroxy-2-benzothiazolyl)-4-thiazole carboxylic acid) to produce light emission may form the basis of the mutant enzymes of the invention.

By way of example, where the protein has substantially the sequence of luciferase of *Photinus pyralis*, in accordance with the invention, at least one of (a) the amino acid residue corresponding to residue 214 in *Photinus pyralis* luciferase has been changed to be other than threonine;
(b) the amino acid residue corresponding to residue 232 in *Photinus pyralis* luciferase has been changed to be other than isoleucine;
(c) the amino acid residue corresponding to residue 295 in *Photinus pyralis* luciferase has been changed to be other than phenylalanine;
(d) the amino acid residue corresponding to amino acid 14 of the *Photinus pyralis* luciferase has been changed to be other than phenylalanine;
(e) the amino acid residue corresponding to amino acid 35 of the *Photinus pyralis* luciferase has been changed to be other than leucine;
(f) the amino acid residue corresponding to amino acid residue 105 of the *Photinus pyralis* luciferase has been changed to be other than alanine;
(g) the amino acid residue corresponding to amino acid residue 234 of the *Photinus pyralis* luciferase has been changed to be other than aspartic acid;
(h) the amino acid residue corresponding to amino acid residue 420 of the *Photinus pyralis* luciferase has been changed to be other than serine;
(i) the amino acid residue corresponding to amino acid residue 310 of the *Photinus pyralis* luciferase has been changed to be other than histidine.

Where the protein has substantially the sequence of *Luciola mingrelica*, *Luciola cruciata* or *Luciola lateralis* enzyme, in accordance with the invention, at least one of
(a) the amino acid residue corresponding to residue 216 of *Luciola mingrelica*, *Luciola cruciata* or *Luciola lateralis* luciferase is other than glycine (for *Luciola mingrelica* based sequences) or aparagine (for *Luciola cruciata* or *Luciola lateralis*) based sequences;
(b) the amino acid residue corresponding to residue 234 of *Luciola mingrelica*, *Luciola cruciata* or *Luciola lateralis* luciferase is other than serine;
(c) amino acid residue corresponding to residue 297 of *Luciola mingrelica*, *Luciola cruciata* or *Luciola lateralis* luciferase is other than leucine;
(d) amino acid residue corresponding to amino acid 16 of *Luciola mingrelica*, or to amino acid 17 of *Luciola cruciata* or *Luciola lateralis* is other than phenylalanine;
(e) amino acid residue corresponding to residue 37 of *Luciola mingrelica*, or 38 of *Luciola cruciata* or *Luciola lateralis* is other than lysine;
(f) amino acid residue corresponding to amino acid residue 106 of *Luciola mingrelica*, or to amino acid 107 of *Luciola cruciata* or *Luciola lateralis* or to amino acid 108 of *Luciola lateralis* gene is other than glycine;
(g) amino acid residue corresponding to amino acid residue 236 of *Luciola mingrelica*, *Luciola cruciata* or *Luciola lateralis* is other than glycine;
(h) amino acid residue corresponding to residue 422 of *Luciola mingrelica*, *Luciola cruciata* or *Luciola lateralis* is other than threonine;
(i) amino acid residue corresponding to amino acid residue 312 of *Luciola mingrelica*, *Luciola cruciata* or *Luciola lateralis* is other than threonine (for *Luciola mingrelica* based sequences) or valine (for *Luciola cruciata* or *Luciola lateralis*) based sequences.

The particular substituted amino acids in any case which give rise to enhanced thermostability can be determined by routine methods as illustrated hereinafter. In each case, different substitutions may result in enhanced thermostability. Substitution may be effected by site-directed mutagenesis of DNA encoding native or suitable mutant proteins as would be understood by the skilled person. The invention in this case is associated with the identification of the positions which are associated with thermostability.

In general however, it may be desirable to consider substituting an amino acid of different properties to the wild type amino acid. Thus hydrophilic amino acid residues may, in some cases be preferably substituted with hydrophobic amino acid residues and vice versa. Similarly, acidic amino acid residues may be substituted with basic residues.

For instance, the protein may comprise a protein having luciferase activity and at least 60% similarity to luciferase from *Photinus pyralis*, *Luciola mingrelica*, *Luciola cruciata* or *Luciola lateralis* enzyme wherein in the sequence of the enzyme, at least one of
(a) the amino acid residue corresponding to residue 214 in *Photinus pyralis* luciferase and to residue 216 of *Luciola mingrelica*, *Luciola cruciata* or *Luciola lateralis* luciferase is mutated and is other than threonine in the case of *Photinus pyralis* luciferase; or
(b) the amino acid residue corresponding to residue 232 in *Photinus pyralis* luciferase and to residue 234 of *Luciola mingrelica*, *Luciola cruciata* or *Luciola lateralis* luciferase is mutated and is other than isoleucine in the case of *Photinus pyralis* luciferase; or
(c) amino acid residue corresponding to residue 295 in *Photinus pyralis* luciferase and to residue 297 of *Luciola mingrelica*, *Luciola cruciata* or *Luciola lateralis* luciferase is mutated and is for example, other than phenylalanine in the case of *Photinus pyralis* luciferase;
and the luciferase enzyme has increased thermostability as compared to the wild-type luciferase.

The sequences of all the various luciferases show that they are highly conserved having a significant degree of similarity between them. This means that corresponding regions among the enzyme sequences are readily determinable by examination of the sequences to detect the most similar regions, although if necessary commercially available software (e.g. "Bestfit" from the University of Wisconsin Genetics Computer Group; see Devereux et al (1984) Nucleic Acid Research 12: 387-395) can be used in order to determine corresponding regions or particular amino acids between the various sequences. Alternatively or additionally, corresponding acids can be determined by reference to L. Ye et al., Biochim. Biophys Acta 1339 (1997) 39-52. The numbering system used in this reference forms the basis of the numbering system used in the present application.

With respect to the possible change of the amino acid residue corresponding to residue 214 in *Photinus pyralis* luciferase, the polar amino acid threonine is suitably replaced with a non polar amino acid such as alanine, glycine, valine, lecine, isoleucine, proline, phenylalanine, methionine, tryptophan or cysteine. A particularly preferred substitution for the threonine residue corresponding to residue 214 in *Photinus pyralis* is alanine. A more preferred substitution is cysteine. However, different polar residues such as asparagine at this position may also enhance the thermostability of the corresponding enzyme having threonine at this position.

Other amino acids which appear at this position in wild-type luciferase enzymes include glycine (*Luciola mingrelica*, *Hotaria paroula*), asparagine (*Pyrophorus plagiophthalamus*, GR, YC, YE and OR, *Luciola cruciata*, *Luciola lateralis*, *Lampyris noctiluca*, *Pyrocelia nayako* *Photinus pennsylvanica* LY, J29) and serine (position 211 in *Phrixothrix* luciferase). These may advantageously be substituted with non-polar or different non-polar side chains such as alanine and cysteine.

As regards the possible change of the amino acid residue corresponding to residue 232 in *Photinus pyralis* luciferase, the nonpolar amino acid isoleucine is suitably replaced with a different non polar amino acid such as alanine, glycine, valine, leucine, proline, phenylalanine, methionine, tryptophan or cysteine. Other amino acids appearing at this position in wild type sequences include serine and asparagine (as well as valine or alanine at corresponding position 229 in Phritothix green and red respectively). Suitably, these polar residues are substituted by non-polar residues such as those outlined above. A particularly preferred substitution for the residue corresponding to residue 232 in *Photinus pyralis* luciferase and to residue 234 of *Luciola mingrelica, Luciola cruciata* or *Luciola lateralis* luciferase is alanine, where this represents a change of amino acid over the wild-type sequence. Changes of the amino acid residue corresponding to residue 295 in *Photinus pyralis* luciferase and to residue 297 of *Luciola mingrelica, Luciola cruciata* or *Luciola lateralis* luciferase, may also affect the thermostability of the protein. (This corresponds to position 292 in *Phrixothix luciferase*.) In general, the amino acid at this position is a non-polar amino acid phenylalanine or leucine. These are suitably changed for different non-polar amino acids. For example, in *Photinus pyralis*, the non-polar amino acid phenylalanine is suitably replaced with a different non polar amino acid, such as alanine, leucine, glycine, valine, isoleucine, proline, methionine, tryptophan or cysteine. A particularly preferred substitution for the phenylalanine residue corresponding to residue 214 in *Photinus pyralis* luciferase is leucine.

Mutation at the amino acid residue corresponding to amino acid 14 of the *Photinus pyralis* luciferase or to amino acid 16 in *Luciola* luciferase, (13 in *Phrixothrix* luciferase) is also possible. This amino acid residue (which is usually phenylalanine, but may also be leucine, serine, arginine or in some instances tyrosine) is suitably changed to a different amino acid, in particular to a different nonpolar amino acid such as alanine, valine, leucine, isoleucine, proline, methionine or tryptophan, preferably alanine.

Mutation at the amino acid residue corresponding to amino acid 35 of the *Photinus pyralis* luciferase or to amino acid residue 37 in *Luciola mingrelica* luciferase (corresponding to amino acid 38 in other *Luciola* spp. And in *Phrixothrix*) may also be effective. This amino acid varies amongst wild type enzymes, which may include leucine (*Photinus pyralis*) but also lysine, histidine, glycine, alanine, glutamine and aspartic acid at this position. Suitably the amino residue at this position is substituted with a non-polar amino acid residue or a different non-polar amino acid such as
such as alanine, valine, phenylalanine, isoleucine, proline, methionine or tryptophan. A preferred amino acid at this position is alanine, where this is different to the wild-type enzyme.

Mutations at the amino acid corresponding to position 14 of the *Photinus pyralis* sequence and/or mutation at the amino acid residue corresponding to amino acid 35 of the *Photinus pyralis* luciferase are preferably not the only mutation in the enzyme.

They are suitably accompanied by others of the mutations defined above, in particular those at positions corresponding to positions 214, 395 or 232 of *Photinus pyralis* luciferase.

Changes of the amino acid residue corresponding to residue 105 in *Photinus pyralis* luciferase and to residue 106 of *Luciola mingrelica, Luciola cruciata* or *Luciola lateralis* luciferase, (102 in *Phrixothrix*) may also affect the thermostability of the protein. In general, the amino acid at this position is a non-polar amino acid alanine or glycine, or serine in *Phrixothrix*. These are suitably changed for different non-polar amino acids. For example, in *Photinus pyralis*, the non-polar amino acid alanine is suitably replaced with a different no npolar amino acid, such as phenylalanine, leucine, glycine, valine, isoleucine, proline, methionine or tryptophan. A particularly preferred substitution for the alanine residue corresponding to residue 105 in *Photinus pyralis* luciferase is valine.

Changes of the amino acid residue corresponding to residue 234 in *Photinus pyralis* luciferase and to residue 236 of *Luciola mingrelica, Luciola cruciata* or *Luciola lateralis* luciferase (231 in *Phrixothrix*), may also affect the thermostability of the protein. In general, the amino acid at this position is aspartic acid or glycine and in some cases, glutamine or threonine. These are suitably changed for non-polar or different non-polar amino acids as appropriate. For example, in *Photinus pyralis*, the amino acid residue is aspartic acid is suitably replaced with a non polar amino acid, such as alanine, leucine, glycine, valine, isoleucine, proline, methionine or tryptophan. A particularly preferred substitution for the phenylalanine residue corresponding to residue 234 in *Photinus pyralis* luciferase is glycine. Where a non-polar amino acid residue such as glycine is present at this position (for example in *Luciola* luciferase), this may be substituted with a different non-polar amino acid.

Changes of the amino acid residue corresponding to residue 420 in *Photinus pyralis* luciferase and to residue 422 of *Luciola mingrelica, Luciola cruciata* or *Luciola lateralis* luciferase (417 in *Phrixothrix* green and 418 in *Phrixothrix* red), may also affect the thermostability of the protein. In general, the amino acid at this position is an uncharged polar amino acid serine or threonine or glycine. These are suitably changed for different uncharged polar amino acids. For example, in *Photinus pyralis*, the serine may be replaced with asparagine, glutamine, threonine or tyrosine, and in particular threonine.

Changes of the amino acid residue corresponding to residue 310 in *Photinus pyralis* luciferase and to residue 312 of *Luciola mingrelica, Luciola cruciata* or *Luciola lateralis* luciferase, may also affect the thermostability of the protein. The amino acid residue at this position varies amongst the known luciferase proteins, being histidine in *Photinus pyralis, Pyrocelia nayalco, Lampyris noctiluca* and some forms of *Photinus pennsylanvanica* luciferase, threonine in *Luciola mingrelica, Hotaria paroula* and *Phrixothix* (where it is amino acid 307) luciferase, valine in *Luciola cruciata* and *Luciola lateralis*, and asparagine in some *Pyrophorus plagiophthalamus* luciferase. Thus, in general, the amino acid at this position is hydrophilic amino acid which may be changed for a different amino acid residue which increases thermostability of the enzyme. A particularly preferred substitution for the histidine residue corresponding to residue 310 in *Photinus pyralis* luciferase is arginine.

Other mutations may also be present in the enzyme. For example, in a preferred embodiment, the protein also has the amino acid at position corresponding to amino acid 354 of the *Photinus pyralis* luciferase (356 in *Luciola* luciferase and 351 in *Phrixothrix*) changed from glutamate, in particular to an amino acid other than glycine, proline or aspartic acid. Suitably, the amino acid at this position is tryptophan, valine, leucine, isoleucine are asparagines, but most preferably is lysine or arginine. This mutation is described in WO 95/25798.

In an alternative preferred embodiment, the protein also has the amino acid at the position corresponding to amino acid 217 in *Luciola luciferase* (215 in *Photinus pyralis*) changed to a hydrophobic amino acid in particular to isoleucine, leucine or valine as described in EP-A-052448.

The proteins may contain further mutations in the sequence provided the luciferase activity of the protein is not unduly compromised. The mutations suitably enhance the properties of the enzyme or better suit it for the intended purpose in some way. This may mean that they result in enhanced thermostability and/or colour shift properties, and/or the $K_m$ for ATP of the enzymes. Examples of mutations which give rise to colour shifts are described in WO95/18853. Mutations which affect $K_m$ values are described for example in WO 96/22376 and International Patent Application No. PCT/GB98/01026 which are incorporated herein by reference.

Proteins of the invention suitably have more than one such mutation, and preferably all three of the mutations described above.

Proteins of the invention include both wild-type and recombinant luciferase enzymes. They have at least 60% similarity to the sequences of *Photinus pyralis, Luciola mingrelica, Luciola cruciata* or *Luciola lateralis* or other luciferase enzymes as discussed above in the sense that at least 60% of the amino acids present in the wild-type enzymes are present in the proteins of the invention. Such proteins can have a greater degree of similarity, in particular at least 70%, more preferably at least 80% and most preferably at least 90% to the wild-type enzymes listed above. Similar proteins of this type include allelic variants, proteins from other insect species as well as recombinantly produced enzymes.

They may be identified for example, in that they are encoded by nucleic acids which hybridise with sequences which encode wild-type enzymes under stringent hybridisation conditions, preferably high stringency conditions. Such conditions would be well understood by the person skilled in the art, and are exemplified for example in Sambrook et al. (1989) Molecular Cloning, Cold Spring Harbor Laboratory Press). In general terms, low stringency conditions can be defined as 3×SCC at about ambient temperature to about 65° C., and high stringency conditions as 0.1×SSC at about 65° C. SSC is the name of a buffer of 0.15M NaCl, 0.015M trisodium citrate. 3×SSC is three times as strong as SSC and so on.

In particular, the similarity of a particular sequence to the sequences of the invention may be assessed using the multiple alignment method described by Lipman and Pearson, (Lipman, D. J. & Pearson, W. R. (1985) Rapid and Sensitive Protein Similarity Searches, Science, vol 227, pp 1435-1441). The "optimised" percentage score should be calculated with the following parameters for the Lipman-Pearson algorithm:ktup=1, gap penalty=4 and gap penalty length=12. The sequence for which similarity is to be assessed should be used as the "test sequence" which means that the base sequence for the comparison, such as the sequence of *Photinus pyralis* or any of the other sequences listed above, as recorded in Ye et al., supra., or in the case of *Phrixotrix*, as described in Biochemistry, 1999, 38, 8271-8279, should be entered first into the algorithm. Generally, *Photinus pyralis* will be used as the reference sequence.

Particular examples of proteins of the invention are wild-type luciferase sequence with the mutations as outlined above. The proteins have at least one and preferably more than one such mutation.

The invention further provides nucleic acids which encode the luciferases as described above. Suitably, the nucleic acids are based upon wild-type sequences which are well known in the art. Suitable mutation to effect the desired mutation in the amino acid sequence would be readily apparent, based upon a knowledge of the genetic code.

The nucleic acids of the invention are suitably incorporated into an expression vector such as a plasmid under the control of control elements such as promoters, enhancers, terminators etc. These vectors can then be used to transform a host cell, for example a prokaryotic or eukaryotic cell such as a plant or animal cell, but in particular a prokaryotic cell such as *E. coli* so that the cell expresses the desired luciferase enzyme. Culture of the thus transformed cells using conditions which are well known in the art will result in the production of the luciferase enzyme which can then be separated from the culture medium. Where the cells are plant or animal cells, plants or animals may be propagated from said cells. The protein may then be extracted from the plants, or in the case of transgenic animals, the proteins may be recovered from milk. Vectors, transformed cells, transgenic plants and animals and methods of producing enzyme by culturing these cells all form further aspects of the invention.

The *Photinus pyralis* T214A mutant luciferase was created by random mutagenesis as described hereinafter. It was found that the T214A single point mutation has greater thermostability than wild type luciferase.

Two new triple mutant luciferases: E354K/T214A/A215L and E354K/T214A/I232A were also prepared and these also have exhibited greater thermostability.

Particular examples of mutant enzymes of *Photinus pyralis* which fall within the scope of the invention include the following:
I232A/E354K
T214A/I232A/E354K
A215L/I232A/E354K
T214A/I232A/E354K/A215L
I232A/E354K/T214A/F295L
I232A/E354K/T214A F295L/F14A/L35A
I232A/E354K/T214A/F295L/F14A/L35A/A215L
A105V
T214A
T214C
T214N
T295L
I232A
F14A
L35A
D234G
S420T
H310R
or equivalents of any of these when derived from the luciferases of other species.

The mutations for the creation of the triple mutant were introduced to the luciferase gene on plasmid pET23 by site-directed mutagenesis, (PCR). The oligonucleotides added to the PCR reaction in order to effect the relevant mutations are given in the Examples below.

It has been reported previously that the effect of point mutations at the 354 and 215 positions are additive. This invention provides the possibility of combining three or more such mutations to provide still greater thermostability.

Thermostable luciferase of the invention will advantageously be employed in any bioluminescent assay which utilises the luciferase/luciferin reaction as a signalling means. There are many such assays known in the literature. The proteins may therefore be included in kits prepared with a view to performing such assays, optionally with luciferin and any other reagents required to perform the particular assay.

BRIEF DESCRIPTION OF THE DRAWINGS

The invention will now be particularly described by way of example with reference to the accompanying diagrammatic drawings in which:

FIG. 5 shows oligonucleotides (SEQ ID NOs: 1-33) used in the preparation of mutant enzymes of the invention.

EXAMPLE 1

Identification of Thermostable Mutant Luciferase

Figure 1A:
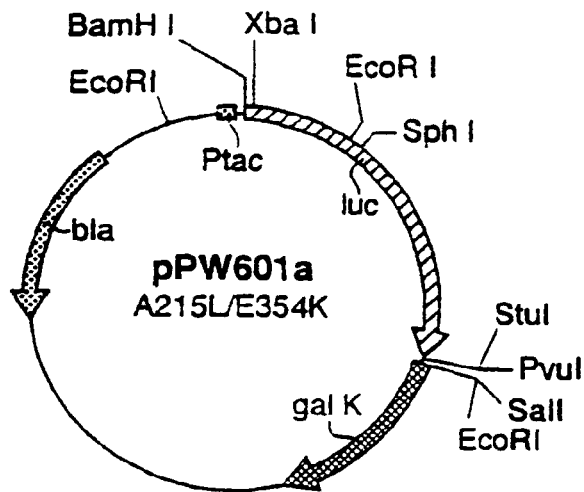
FIGS. 1A and 1B illustrate the plasmids used in the production of mutants in accordance with the invention.
Figure 1A:
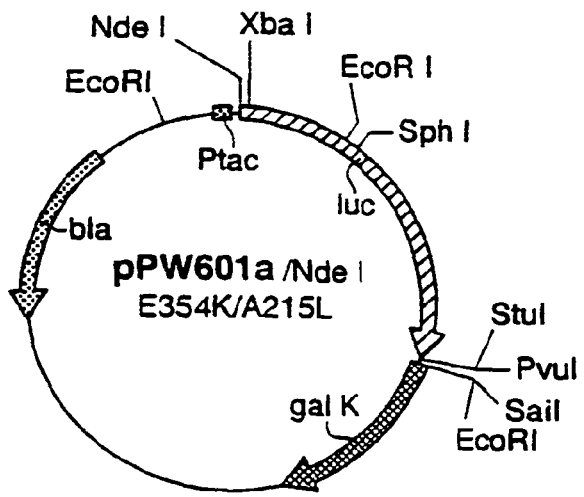
Figure 1A:
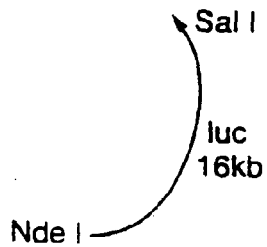
Figure 1B:
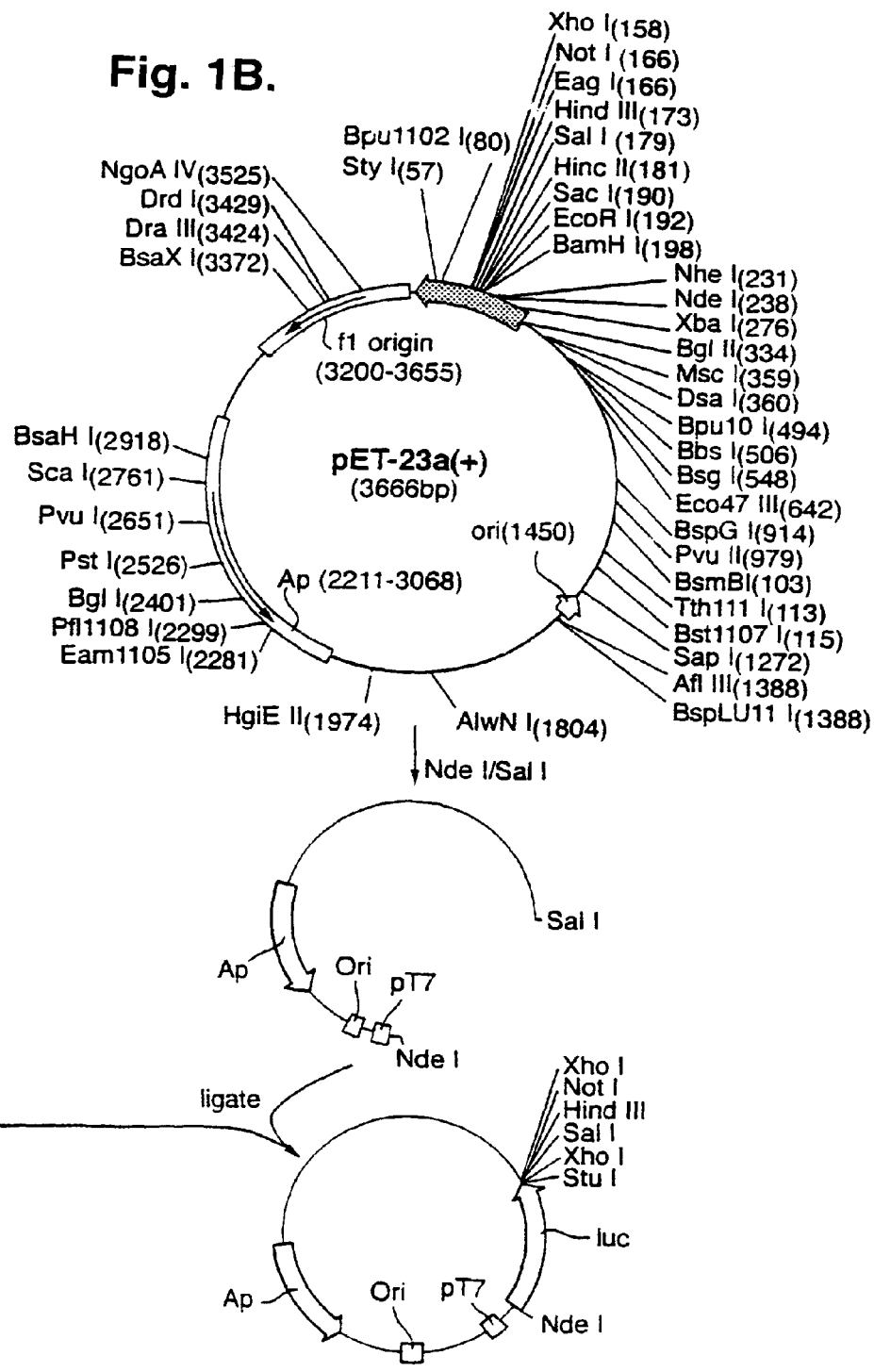

The error-prone PCR was based on the protocol devised by Fromant et al., Analytical Biochemistry, 224, 347-353 (1995).

The dNTP mix in this reaction was:
35 mM dTTP
12.5 mM dGTP
22.5 mM dCTP
14 mM dATP The PCR conditions were:
0.5 µl (50 ng) plasmid pPW601a J54*
5.0 µl 10×KC1 reaction buffer
1 µl each of W56 and W57+ (60 pmoles of each primer)
1 µl BIOTAQ (thermostable) DNA polymerase (5U)
2 µl dNTPs (see above)
1.76 µl MgCl$_2$ (50 mM stock)
1 µl mNCl$_2$ (25 mM stock) [final concentration in reaction=3.26 mM]
36.7 µl dH$_2$O

*Plasmid pPW601aJ54 is a mutated version of pPW601a (WO 95/25798) where an NdeI site has been created within the 3 bases prior to the ATG start codon. This allows for easy cloning from pPW601a into the pET23 vector.

+Primer Sequences:

```
W56:
                                      (SEQ ID NO: 34)
5' - AAACAGGGACCCATATGGAAGACGC - 3'

W57:
                                      (SEQ ID NO: 35)
5' - AATTAACTCGAGGAATTTCGTCATCGCTGAATACAG - 3')
```

Cycling parameters were:
94° C.-5 min
Then 12× cycles of: 94° C.-30s
55° C.-30s
72° C.-5 min
72° C.-10 min The PCR products were purified from the reaction mix using a Clontech ADVANTAGE PCR-pure kit. An aliquot of the purified products was then digested with the restriction enzymes NdeI and XhoI. The digested PCR products were then "cleaned up" with the ADVANTAGE kit and ligated into the vector pET23a which had been digested with the same enzymes.

Ligation Conditions:
4 µl pET23a (56 ng)
5 µl PCR products (200 ng)
3 µl 5× Gibco BRL ligase reaction buffer
1 µl Gibco BRL ligase (10U)
2 µl dH$_2$O The ligation was carried out overnight at 16° C.

The ligated DNAs were then purified using the ADVANTAGE kit and then electroporated into electrocompetent E. coli HB101 cells (1 mm cuvettes, 1.8 Kv).

Eleven electroporations were performed and the cells were then added to 40 ml of TY broth containing 50 µg/ml ampicillin. The cells were then grown overnight at 37° C. The entire 50 ml of culture grown overnight was used to purify plasmid DNA. This is the library.

Screening the Library

An aliquot of the plasmid library was used to electroporate E. coli BL21 DE3 cells. These cells were then plated onto LB agar containing 50 µg/ml ampicillin and grown overnight at 37° C.

The next day, colonies were picked and patched onto nylon filters on LB agar+amp plates and growth continued overnight at 37° C. The next day, filters were overlaid with a solution of luciferin—500 µM in 100 mM sodium citrate pH5.0. The patches were then viewed in a darkroom. One colony/patch was picked from 200 for further analysis.

Characterisation of the Thermostable Mutant

The E. coli clone harbouring the mutant plasmid was isolated. Plasmid DNA was prepared for ABI sequencing. The entire open reading frame encoding luciferase was sequenced using 4 different oligonucleotide primers. Sequencing revealed a single point mutation at nt 640 (A→G). Giving a codon change of ACT (T) to GCT (A) at amino acid position 214.

EXAMPLE 2

Preparation of Triple Mutant Enzyme

A mutagenic oligonucleotide was then used to create this same mutation in pMOD1 (A215L/E354K) to create a triple mutant pMOD2 (A215L/E354K/T214A). This mutation also creates a unique SacI/SstI site in pMOD1.

EXAMPLE 3

Preparation of Further Triple Mutant Enzyme

The following primers were used to create the triple mutant T214A/I232A/E354K using a standard PCR reaction and with the pET23 plasmid with the T214A mutation as template:

```
                                      (SEQ ID NO: 26)
CTGATTACACCCAAGGGGATG
E354K-sense (SEQ ID NO: 27)
CATCCCCCTTGGGTGTAATCAG
E354K-antisense (SEQ ID NO: 30)
GCAATCAAATCGCTCCGGATACTGC
I232A-sense (SEQ ID NO: 31)
GCAGTATCCGGAGCGATTTGATTGC
I232A-antisense
```

EXAMPLE 4

Identification of Thermostable 295 Mutant

The F295 mutant was created using the error-prone PCR method described by Fromant et al., Analytical Biochemistry, vol 224, 347-353 (1995). The PCR conditions used were as follows:
0.5 µl (50 ng) plasmid pET23
5.0 µl 10×KCI reaction buffer
1 µl primer 1-60 pmoles of each primer
1 µl primer 2
1 µl BIOTAQ (thermostable) DNA polymerase (5U)
2 µl dNTPs, in mixture 35 mM dTTP, 12.5 mM dGTP, 22.5 mM dCTP,
14 mM dATP
1.76 µl MgCl$_2$ (50 mM stock)
1 µl MnCl$_2$ (25 mM stock) [final concentration in reaction=3.26 mM]
36.7 µl dH$_2$O

```
Primer 1 =
                                       (SEQ ID NO: 34)
5' - AAACAGGGACCCATATGGAAGACGC - 3'

Primer 2 =
                                       (SEQ ID NO: 35)
5' - AATTAACTCGAGGAATTTCGTCATCGCTGAATACAG - 3'
```

The cycling parameters were:
94° C. for 5 min
15 cycles of: 30 s@ 94° C.
  30 s@ 55° C.
  5 Min@ 72° C.
then 10 min at 72° C.

The PCR products were purified from the reaction mix using a Clontech ADVANTAGE PCR-Pure kit. An aliquot of the purified products was then digested with the restriction enzymes NdeI and XhoI. The digested PCR products were then "cleaned up" with the ADVANTAGE kit and ligated into the vector pET23a, which had been digested with the same enzymes.

The ligation conditions were as follows:
56 ng pET23a
200 ng PCR products
3 µl 5× Gibco BRL ligase reaction buffer
1 µl Gibco BRL ligase (10U)
volume made up to 10 µl with dH$_2$O The ligation was carried out overnight at 16° C.

The ligated DNAs were then purified using the Advantage™ kit and then electroporated into electrocompetent *Escherichia coli* DH5α cells (1 mm cuvettes, 1.8 kV). 1 ml of SOC broth was added to each electroporation and the cells allowed to recover and express antibiotic resistance genes encoded by the plasmid. Aliquots of the library were inoculated onto LB agar containing 50 µg/ml ampicillin and the bacteria were grown overnight at 37° C. Nylon filter discs were then overlaid onto the agar plates and the colonies transferred to fresh plates. The original plates were left at room temperature for the colonies to re-grow. The plates with the nylon filters were incubated at 42° C. for 2 h before plates were sprayed with 500 µM luciferin in 100 mM citrate buffer pH5.0 and viewed in a darkroom.

Three thermostable colonies were selected on the basis that they still glowed after 2 h at 42° C. Plasmid DNA was isolated from these clones and sequenced, and this revealed the F295L mutation in each case.

EXAMPLE 5

Other mutants of the invention were produced by PCR using appropriate combinations of the oligonucleotides listed above as well as the following:

```
                                        (SEQ ID NO: 5)
GAAAGGCCCGGCACCAGCCTATCCTCTAGAGG
F14A-sense (SEQ ID NO: 6)
CCTCTAGCGGATAGGCTGGTGCCGGGCCTTTC
F14A-antisense (SEQ ID NO: 9)
GAGATACGCCGCGGTTCCTGG
L35A-sense (SEQ ID NO: 10)
CCAGGAACCGCGGCGTATCTC
L35A-antisense
```

EXAMPLE 6

Purification of Luciferase and Heat Inactivation Studies

Cells expressing the recombinant mutant luciferases were cultured, disrupted and extracted as described in WO 95/25798 to yield cell free extracts of luciferase.

Eppendorf tubes containing the cell free extracts were incubated generally at 40° C. unless otherwise stated. Purified preparations of wild type luciferases (for comparative purposes were incubated in thermostability buffer comprising 50 mM potassium phosphate buffer pH7.8 containing 10% saturated ammonium sulphate, 1 mM dithiothreitol and 0.2% bovine serum albumin (BSA). At set times a tube was removed and cooled in an ice/water bath prior to assay with remaining assayed activity being calculated as a percentage of the initial activity or relative bioluminesce.

Figure 2:
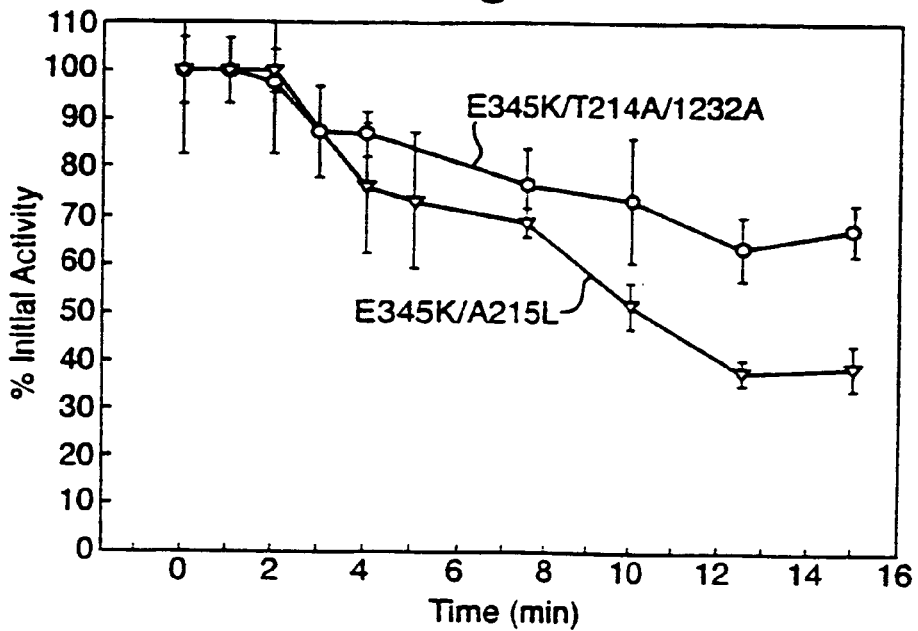
FIG. 2 shows the results of heat inactivation studies on luciferases including luciferases of the invention.

The results are illustrated in FIGS. 2 and 3 hereinafter. It can be seen from FIG. 2 that luciferase mutants of the invention have improved thermostability compared with the previously known mutants.

The dramatic increase in stability over wild-type luciferase (RWT) is clear from FIG. 3.

EXAMPLE 7

Investigations into the Activity of 214 Mutants

A library of 214 mutants was prepared using site-directed mutagenesis using cassette oligos (FIG. 5) and thermostable mutants selected and tested as described in Example 1. Three particularly thermostable mutants were characterised by sequencing as described in Example 1 as T214A, T214C and T214N.

O/N cultures of *E. coli* XL1-Blue harbouring plasmids encoding T214, T214A, T214C and T214N were lysed using the *Promega lysis* buffer. 50 µl of liquid extracts were then heat inactivated at 37° C. and 40° C. over various time points. Aliquots 10 µl of heated extract were then tested in the Promega live assay buffer (100 µl).

The results are shown in the following Tables

|  | 0 | 4 min | 8 min | 22 min | (37° C.) |
|---|---|---|---|---|---|
| rwt T214 | 11074 | 5561 | 2555 | 343 | RLU |
| T214C | 106449 | 92471 | 90515 | 78816 | RLU |
| T214A | 63829 | 52017 | 45864 | 35889 | RLU |
| T214N | 60679 | 49144 | 41736 | 29488 | RLU |

|  | % remaining activity 37° C. | | | |
|---|---|---|---|---|
| rwt T214 | 100 | 50.2 | 23.1 | 3.1 |
| T214C | 100 | 86.9 | 85.0 | 74.0 |
| T214A | 100 | 81.5 | 71.8 | 56.2 |
| T214N | 100 | 81.0 | 68.8 | 48.6 |

The experiment was repeated at 40° C. with the 3 mutants

|  | 0 | 4 min | 8 min | 16 min |  |
|---|---|---|---|---|---|
| T214C | 104830 | 79365 | 72088 | 56863 | RLU |
| T214A | 64187 | 43521 | 28691 | 14547 | RLU |
| T214N | 60938 | 38359 | 25100 | 12835 | RLU |

|  | % remaining activity 40° C. | | |
|---|---|---|---|
|  | 0 | 4 min | 8 min | 16 min |
| T214C | 100 | 73.7 | 68.8 | 54.2 |
| T214A | 100 | 67.8 | 44.7 | 22.7 |
| T214N | 100 | 63.0 | 41.2 | 21.1 |

These results indicate that T214C is significantly more thermostable than either r-wt or T214A or N. This change in properties is unexpected as it is usually expected that the more cysteine residues that are present, the worse the thermostability.

EXAMPLE 8

Investigation of Other Point Mutations

Figure 4:
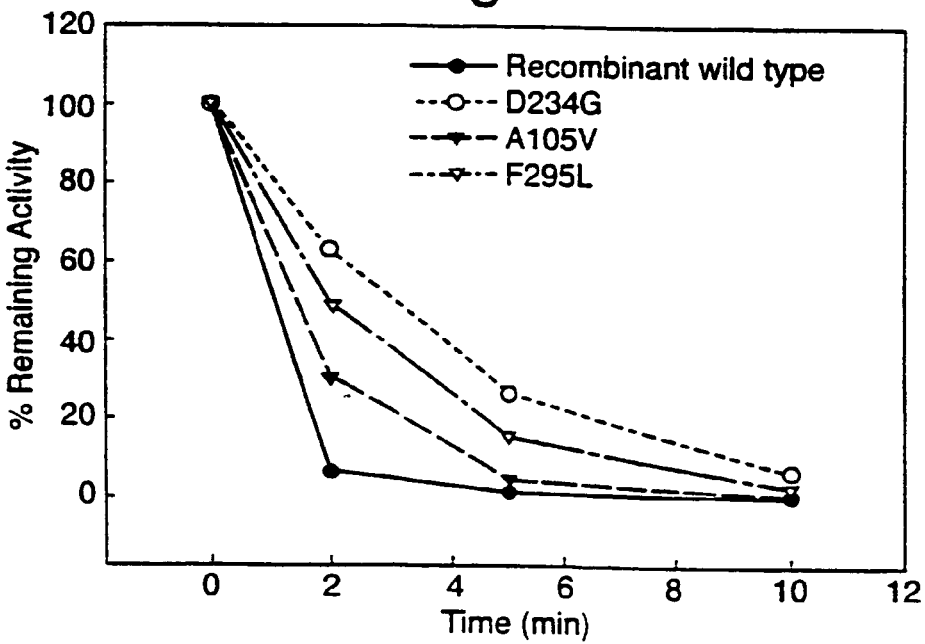
FIG. 4 shows the results of thermostability experiments on other luciferase mutants.
Figure 3A:
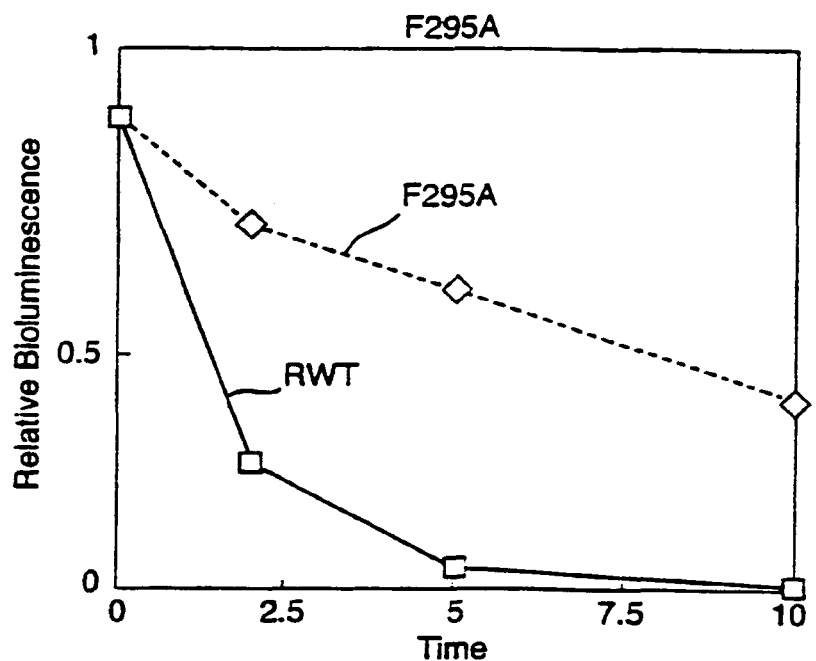
FIGS. 3A-3H show the results of thermostability experiments on various luciferase mutants.
Figure 3B:
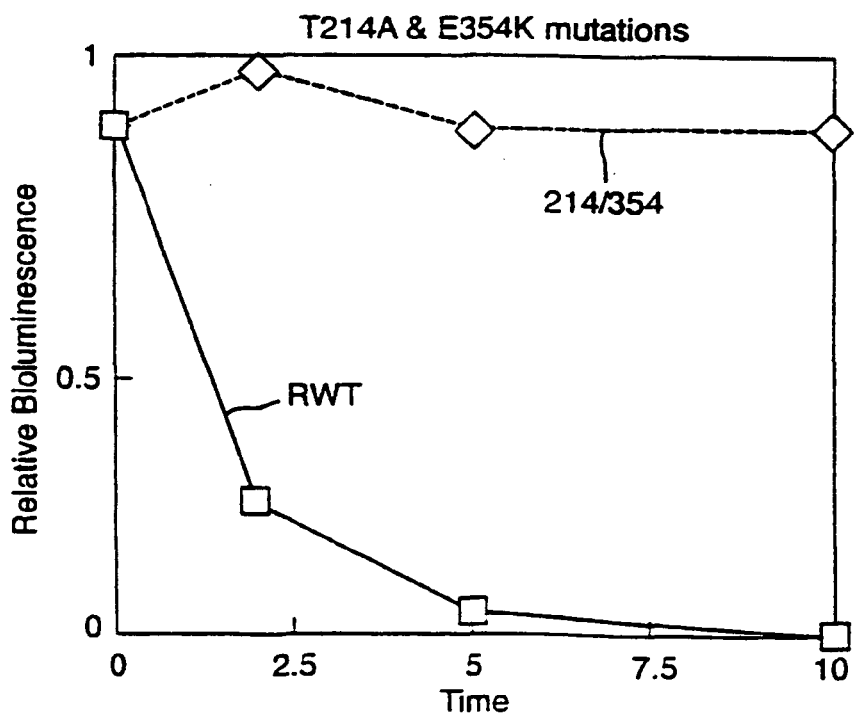
Figure 3C:
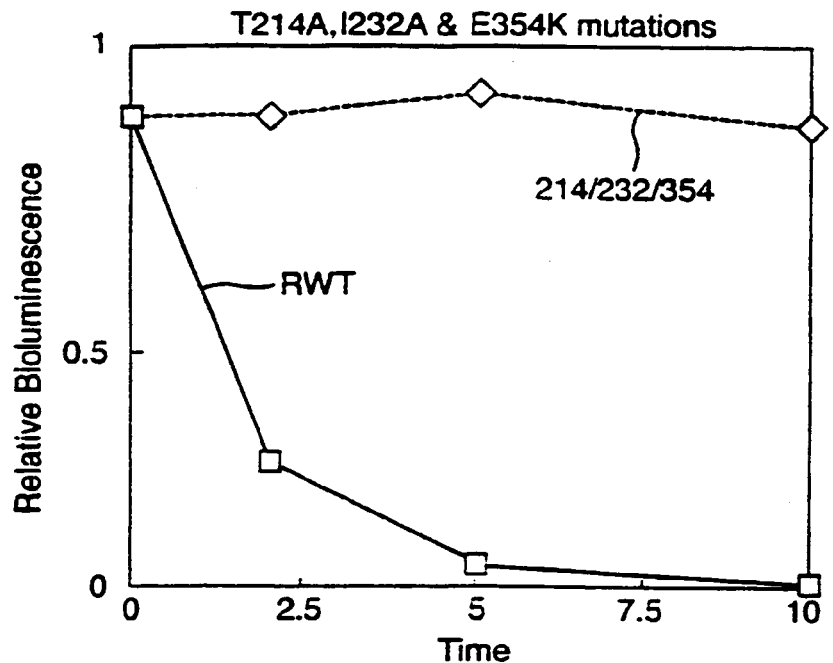
Figure 3D:
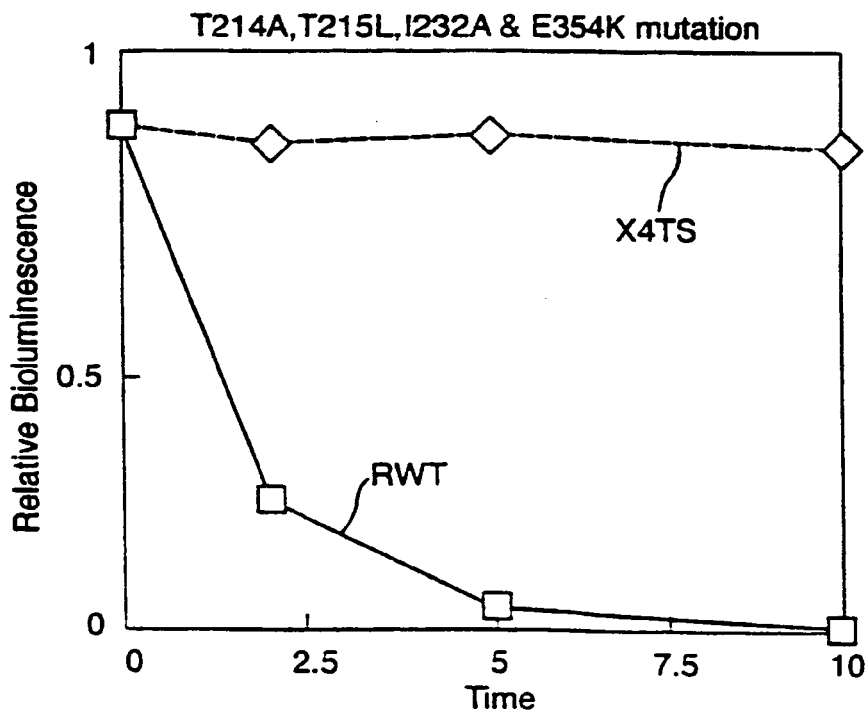
Figure 3E:
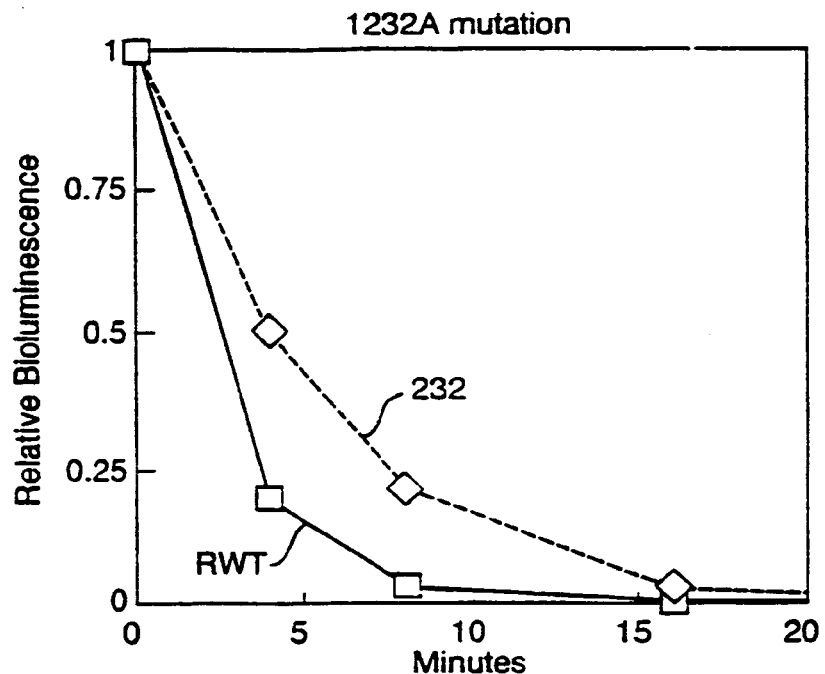
Figure 3F:
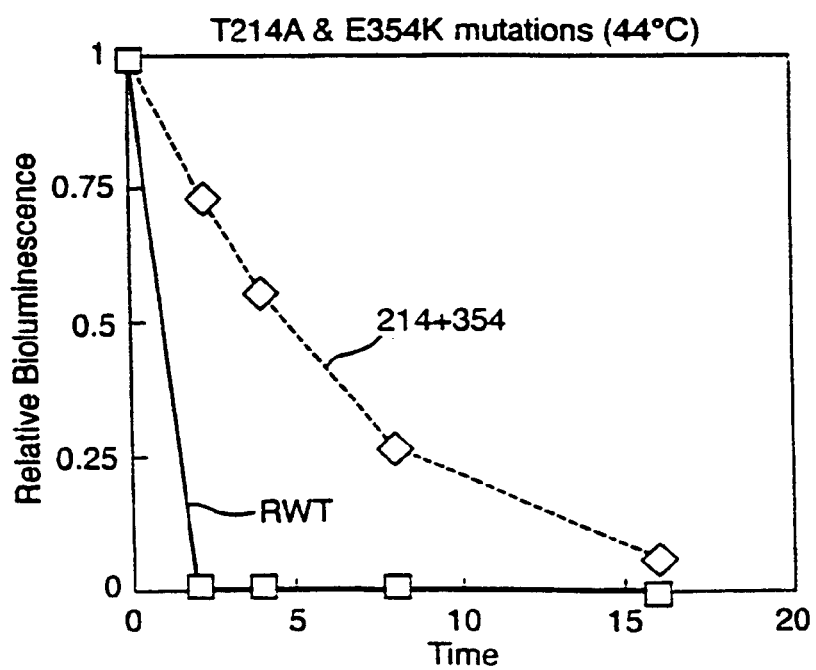
Figure 3G:
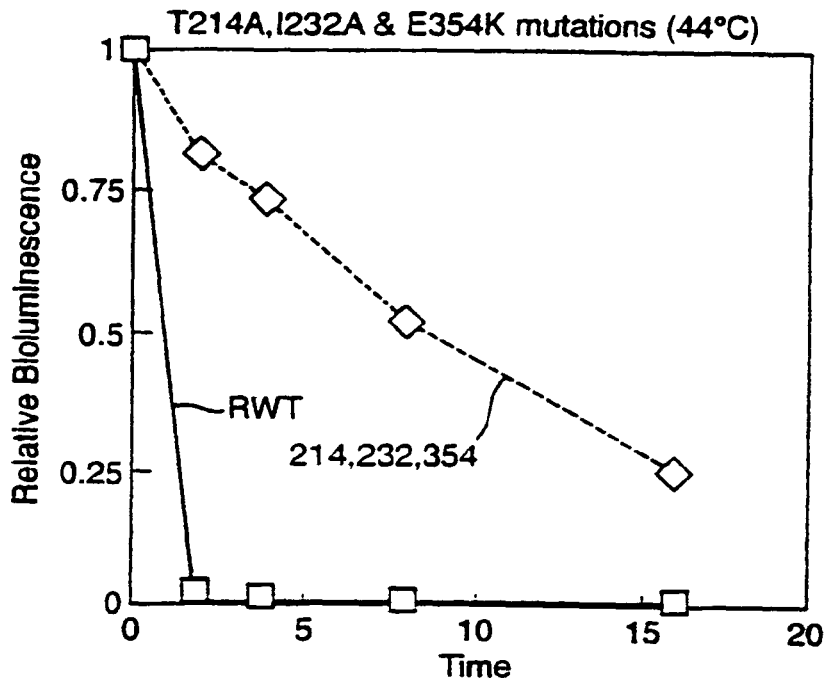
Figure 3H:
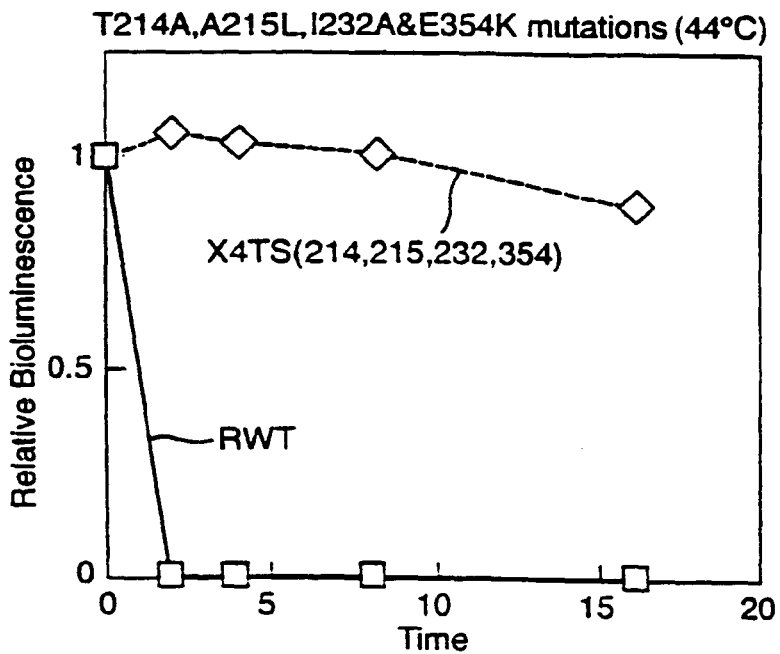

A series of other *Photinus pyralis* mutants with single point mutations were prepared using random error-prone PCR (FIG. 5). Following, screening and sequencing of the mutants generated, the sequencing was checked using site-directed mutagenesis followed by further sequencing. These were D234G, A105V and F295L. The thermostability of these mutants as well as recombinant wild-type *Photinus pyralis* luciferase was tested. Protein samples in *Promega lysis* buffer were incubated at 37° C. for 10 minutes and their activity assayed after 2, 5 and 10 minutes. The results, showing that each mutation produced enhanced thermostability over wild type, is shown in FIG. 4.

The invention claimed is:

1. An isolated recombinant luciferase having luciferase activity and comprising a variant of wild-type *Photinus pyralis* luciferase of SEQ ID NO: 37, wherein the amino acid sequence of said recombinant luciferase has no more than 50 amino acid differences as compared to the amino acid sequence of SEQ ID NO: 37, wherein the amino acid residue of the recombinant luciferase corresponding to position 295 of SEQ ID NO:37 is leucine, the amino acid residue of the recombinant luciferase corresponding to position 214 of SEQ ID NO:37 is an amino acid residue other than threonine, the amino acid residue of the recombinant luciferase corresponding to position 232 of SEQ ID NO:37 is an amino acid residue other than isoleucine, and the amino acid residue of the recombinant luciferase corresponding to position 354 of SEQ ID NO:37 is an amino acid residue other than glutamic acid, and wherein the recombinant luciferase has increased thermostability as compared to the wild-type *Photinus pyralis* luciferase of SEQ ID NO:37.

2. The recombinant luciferase of claim 1, further comprising an amino acid other than phenylalanine at the amino acid residue corresponding to position 14 of SEQ ID NO:37.

3. The recombinant luciferase of claim 2, wherein the amino acid residue corresponding to position 14 of SEQ ID NO:37 is alanine.

4. The recombinant luciferase of claim 1, further comprising an amino acid other than leucine at the amino acid residue corresponding to position 35 of SEQ ID NO:37.

5. The recombinant luciferase of claim 4, wherein the amino acid residue corresponding to position 35 of SEQ ID NO:37 is alanine.

6. The recombinant luciferase of claim 1, wherein the amino acid at the residue corresponding to position 354 of SEQ ID NO:37 is lysine.

7. The recombinant luciferase of claim 1, further comprising an amino acid other than alanine at the amino acid residue corresponding to position 215 of SEQ ID NO:37.

8. The recombinant luciferase of claim 7, wherein the amino acid residue corresponding to position 215 of SEQ ID NO:37 is lysine.

9. The recombinant luciferase of claim 1, wherein the amino acid residue corresponding to position 214 of SEQ ID NO:37 is alanine, the amino acid residue corresponding to position 232 of SEQ ID NO:37 is alanine and the amino acid residue corresponding to position 354 of SEQ ID NO:37 is lysine.

10. The recombinant luciferase of claim 1, further comprising an amino acid other than phenylalanine at the amino acid residue corresponding to position 14 of SEQ ID NO:37 and an amino acid other than leucine at the amino acid residue corresponding to position 35 of SEQ ID NO:37.

11. The recombinant luciferase of claim 10, wherein the amino acid residue corresponding to position 14 of SEQ ID NO:37 is alanine and the amino acid residue corresponding to position 35 of SEQ ID NO:37 is alanine.

12. The recombinant luciferase of claim 10, further comprising an amino acid other than alanine at the amino acid residue corresponding to position 215 of SEQ ID NO:37.

13. The recombinant luciferase of claim 12, wherein the amino acid residue corresponding to position 215 of SEQ ID NO:37 is leucine.

14. A bioluminescent assay comprising the steps of contacting the recombinant luciferase of claim 1 with luciferin and detecting bioluminescence.

15. A kit comprising the recombinant luciferase of claim 1.

* * * * *

SEQUENCE LISTING

<160> NUMBER OF SEQ ID NOS: 42

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 1
cgccggtgag ctccccgccg ccg                                          23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 2
cggcggcggg gagctcaccg gcg                                          23

<210> SEQ ID NO 3
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 3
cgaacacttc ttcatcgttg accgccttaa gtctttaatt aaatacaaag g           51

<210> SEQ ID NO 4

```
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 4
cctttgtatt taattaaaga cttaaggcgg tcaactatga agaagtgttc g          51

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 5
gaaaggcccg gcaccagcct atcctctaga gg                               32

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 6
cctctagcgg ataggctggt gccgggcctt tc                               32

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 7
ccataaattt accgaattcg tcgacttcga tcgagg                           36

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 8
gtgtggaatt gtgagcgg                                               18

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 9
gagatacgcc gcggttcctg g                                           21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 10
```
ccaggaaccg cggcgtatct c                                         21

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 11
ccctattttc attcctggcc aaaagcactc                                30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 12
gagtgctttt ggccaggaat gaaaataggg                                30

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 13
ccgcatagag ctctctgcgt cagattc                                   27

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 14
gaatctgacg cagagagctc tatgcgg                                   27

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 15
gttgaccgct tgggatcctt aattaaatac                                30

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 16
gtatagattt gaaaagagc tg                                         22

<210> SEQ ID NO 17
<211> LENGTH: 22
<212> TYPE: DNA
<213> ORGANISM: Artificial Sequence
<220> FEATURE:

```
<223> OTHER INFORMATION: Description of Artificial Sequence: Primer

<400> SEQUENCE: 17 cagctcttt tcaaatctat ac                                              22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 18
ggctacatac tggagacata gc                                             22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 19
gctatgtctc cagtatgtag cc                                             22

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 20
gcagttgcgc ccgtgaacga c                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 21
gtcgttcacg ggcgcaactg c                                              21

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 22
caaatcattc cgggtactgc gattttaag                                      29

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 23
cttaaaatcg cagtacccgg aatgatttg                                      29

<210> SEQ ID NO 24
```

```
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 24
ccgcatagaa ctctctgcgt cagattc                                         27

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 25
gaatctgacg cagagagttc tatgcgc                                         27

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 26
ctgattacac ccaaggggga tg                                              22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 27
catccccctt gggtgtaatc ag                                              22

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (15)..(17)
<223> OTHER INFORMATION: a, g, c or t

<400> SEQUENCE: 28
cccttccgca tagannngcc tgcgtcagt                                       29

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (13)..(15)
<223> OTHER INFORMATION: a, g, c or t

<400> SEQUENCE: 29
actgacgcag gcnnntctat gcggaaggg                                       29

<210> SEQ ID NO 30
```

```
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 30
gcaatcaaat cgctccggat actgc                                          25

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 31
gcagtatccg gagcgatttg attgc                                          25

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 32
ccattccatc aaggttttgg                                                20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 33
ccaaaacctt gatggaatgg                                                20

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 34
aaacagggac ccatatggaa gacgc                                          25

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 35
aattaactcg aggaatttcg tcatcgctga atacag                              36

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 36
```
ccctattttc attcctggcc aaaagcactg                    30

<210> SEQ ID NO 37
<211> LENGTH: 550
<212> TYPE: PRT
<213> ORGANISM: Photinus pyralis

<400> SEQUENCE: 37

```
Met Glu Asp Ala Lys Asn Ile Lys Lys Gly Pro Ala Pro Phe Tyr Pro
 1               5                  10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
```

-continued

```
            370                 375                 380
Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp His Phe
                420                 425                 430

Phe Ile Val Asp Arg Leu Lys Ser Leu Ile Lys Tyr Lys Gly Tyr Gln
                435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
                500                 505                 510

Arg Gly Gly Val Val Phe Val Asp Glu Val Pro Lys Gly Leu Thr Gly
                515                 520                 525

Lys Leu Asp Ala Arg Lys Ile Arg Glu Ile Leu Ile Lys Ala Lys Lys
530                 535                 540

Gly Gly Lys Ser Lys Leu
545                 550

<210> SEQ ID NO 38
<211> LENGTH: 550
<212> TYPE: PRT
<213> ORGANISM: Photinus pyralis
<220> FEATURE:
<221> NAME/KEY: VARIANT
<222> LOCATION: (214)
<223> OTHER INFORMATION: xaa=an amino acid other than Thr

<400> SEQUENCE: 38

Met Glu Asp Ala Lys Asn Ile Lys Lys Gly Pro Ala Pro Phe Tyr Pro
 1               5                  10                  15

Leu Glu Asp Gly Thr Ala Gly Glu Gln Leu His Lys Ala Met Lys Arg
                20                  25                  30

Tyr Ala Leu Val Pro Gly Thr Ile Ala Phe Thr Asp Ala His Ile Glu
                35                  40                  45

Val Asn Ile Thr Tyr Ala Glu Tyr Phe Glu Met Ser Val Arg Leu Ala
50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
                100                 105                 110

Glu Leu Leu Asn Ser Met Asn Ile Ser Gln Pro Thr Val Val Phe Val
                115                 120                 125

Ser Lys Lys Gly Leu Gln Lys Ile Leu Asn Val Gln Lys Lys Leu Pro
130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175
```

```
Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Xaa Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
                260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ser Lys Leu
545                 550

<210> SEQ ID NO 39
<211> LENGTH: 550
<212> TYPE: PRT
<213> ORGANISM: Photinus pyralis
<220> FEATURE:
<221> NAME/KEY: VARIANT
<222> LOCATION: (214)
```

<223> OTHER INFORMATION: Xaa=Cys, Ala or Asn

<400> SEQUENCE: 39

```
Met Glu Asp Ala Lys Asn Ile Lys Lys Gly Pro Ala Pro Phe Tyr Pro
1               5                   10                  15
Leu Glu Asp Gly Thr Ala Gly Glu Gln Leu His Lys Ala Met Lys Arg
            20                  25                  30
Tyr Ala Leu Val Pro Gly Thr Ile Ala Phe Thr Asp Ala His Ile Glu
        35                  40                  45
Val Asn Ile Thr Tyr Ala Glu Tyr Phe Glu Met Ser Val Arg Leu Ala
    50                  55                  60
Glu Ala Met Lys Arg Tyr Gly Leu Asn Thr Asn His Arg Ile Val Val
65                  70                  75                  80
Cys Ser Glu Asn Ser Leu Gln Phe Phe Met Pro Val Leu Gly Ala Leu
                85                  90                  95
Phe Ile Gly Val Ala Val Ala Pro Ala Asn Asp Ile Tyr Asn Glu Arg
            100                 105                 110
Glu Leu Leu Asn Ser Met Asn Ile Ser Gln Pro Thr Val Val Phe Val
        115                 120                 125
Ser Lys Lys Gly Leu Gln Lys Ile Leu Asn Val Gln Lys Lys Leu Pro
    130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
            180                 185                 190
Ala Leu Ile Met Asn Ser Ser Gly Ser Thr Gly Leu Pro Lys Gly Val
        195                 200                 205
Ala Leu Pro His Arg Xaa Ala Cys Val Arg Phe Ser His Ala Arg Asp
    210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
            260                 265                 270
Phe Leu Arg Ser Leu Gln Asp Tyr Lys Ile Gln Ser Ala Leu Leu Val
        275                 280                 285
Pro Thr Leu Phe Ser Phe Phe Ala Lys Ser Thr Leu Ile Asp Lys Tyr
    290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
            340                 345                 350
Pro Glu Gly Asp Asp Lys Pro Gly Ala Val Gly Lys Val Val Pro Phe
        355                 360                 365
Phe Glu Ala Lys Val Val Asp Leu Asp Thr Gly Lys Thr Leu Gly Val
    370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
```

```
                       405                 410                 415
Trp Leu His Ser Gly Asp Ile Ala Tyr Trp Asp Glu Asp His Phe
            420                 425                 430

Phe Ile Val Asp Arg Leu Lys Ser Leu Ile Lys Tyr Lys Gly Tyr Gln
            435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
530                 535                 540

Gly Gly Lys Ser Lys Leu
545                 550

<210> SEQ ID NO 40
<211> LENGTH: 550
<212> TYPE: PRT
<213> ORGANISM: Photinus pyralis
<220> FEATURE:
<221> NAME/KEY: VARIANT
<222> LOCATION: (214)
<223> OTHER INFORMATION: Xaa=Ala
<220> FEATURE:
<221> NAME/KEY: VARIANT
<222> LOCATION: (354)
<223> OTHER INFORMATION: Xaa=Lys

<400> SEQUENCE: 40

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190
```

```
Ala Leu Ile Met Asn Ser Ser Gly Ser Thr Gly Leu Pro Lys Gly Val
            195                 200                 205

Ala Leu Pro His Arg Xaa Ala Cys Val Arg Phe Ser His Ala Arg Asp
            210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
            245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
            275                 280                 285

Pro Thr Leu Phe Ser Phe Phe Ala Lys Ser Thr Leu Ile Asp Lys Tyr
            290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
            325                 330                 335

Arg Gln Gly Tyr Gly Leu Thr Glu Thr Thr Ser Ala Ile Leu Ile Thr
            340                 345                 350

Pro Xaa Gly Asp Asp Lys Pro Gly Ala Val Gly Lys Val Val Pro Phe
            355                 360                 365

Phe Glu Ala Lys Val Val Asp Leu Asp Thr Gly Lys Thr Leu Gly Val
            370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
            405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
            435                 440                 445

Val Ala Pro Ala Glu Leu Glu Ser Ile Leu Leu Gln His Pro Asn Ile
            450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
            485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
            530                 535                 540

Gly Gly Lys Ser Lys Leu
545                 550

<210> SEQ ID NO 41
<211> LENGTH: 550
<212> TYPE: PRT
<213> ORGANISM: Photinus pyralis
<220> FEATURE:
<221> NAME/KEY: VARIANT
<222> LOCATION: (214)
<223> OTHER INFORMATION: Xaa=Ala
<220> FEATURE:
```

```
<221> NAME/KEY: VARIANT
<222> LOCATION: (232)
<223> OTHER INFORMATION: Xaa=Ala
<220> FEATURE:
<221> NAME/KEY: VARIANT
<222> LOCATION: (354)
<223> OTHER INFORMATION: Xaa=Lys

<400> SEQUENCE: 41

Met Glu Asp Ala Lys Asn Ile Lys Lys Gly Pro Ala Pro Phe Tyr Pro
 1               5                   10                  15

Leu Glu Asp Gly Thr Ala Gly Glu Gln Leu His Lys Ala Met Lys Arg
                20                  25                  30

Tyr Ala Leu Val Pro Gly Thr Ile Ala Phe Thr Asp Ala His Ile Glu
            35                  40                  45

Val Asn Ile Thr Tyr Ala Glu Tyr Phe Glu Met Ser Val Arg Leu Ala
 50                  55                  60

Glu Ala Met Lys Arg Tyr Gly Leu Asn Thr Asn His Arg Ile Val Val
 65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Xaa Ala Cys Val Arg Phe Ser His Ala Arg Asp
    210                 215                 220

Pro Ile Phe Gly Asn Gln Ile Xaa Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Xaa Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
```

```
                    370                 375                 380
Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp His Phe
                420                 425                 430

Phe Ile Val Asp Arg Leu Lys Ser Leu Ile Lys Tyr Lys Gly Tyr Gln
                435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
                500                 505                 510

Arg Gly Gly Val Val Phe Val Asp Glu Val Pro Lys Gly Leu Thr Gly
                515                 520                 525

Lys Leu Asp Ala Arg Lys Ile Arg Glu Ile Leu Ile Lys Ala Lys Lys
530                 535                 540

Gly Gly Lys Ser Lys Leu
545                 550

<210> SEQ ID NO 42
<211> LENGTH: 550
<212> TYPE: PRT
<213> ORGANISM: Photinus pyralis
<220> FEATURE:
<221> NAME/KEY: VARIANT
<222> LOCATION: (214)
<223> OTHER INFORMATION: Xaa=Ala
<220> FEATURE:
<221> NAME/KEY: VARIANT
<222> LOCATION: (215)
<223> OTHER INFORMATION: Xaa=Leu
<220> FEATURE:
<221> NAME/KEY: VARIANT
<222> LOCATION: (232)
<223> OTHER INFORMATION: Xaa=Ala
<220> FEATURE:
<221> NAME/KEY: VARIANT
<222> LOCATION: (354)
<223> OTHER INFORMATION: Xaa=Lys

<400> SEQUENCE: 42

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
                20                  25                  30

Tyr Ala Leu Val Pro Gly Thr Ile Ala Phe Thr Asp Ala His Ile Glu
                35                  40                  45

Val Asn Ile Thr Tyr Ala Glu Tyr Phe Glu Met Ser Val Arg Leu Ala
50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
                100                 105                 110
```

-continued

```
Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Xaa Xaa Cys Val Arg Phe Ser His Ala Arg Asp
    210                 215                 220

Pro Ile Phe Gly Asn Gln Ile Xaa Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Xaa Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
530                 535                 540
```

```
Gly Gly Lys Ser Lys Leu
545                 550
```